(12) United States Patent
Zi et al.

(10) Patent No.: US 11,998,232 B2
(45) Date of Patent: Jun. 4, 2024

(54) THERAPEUTIC DEVICE, THERAPEUTIC SYSTEM AND THERAPEUTIC METHOD FOR MYOCARDIUM REPAIR

(71) Applicant: DEKE MEDTECH (HANGZHOU) INC., Hangzhou (CN)

(72) Inventors: Zhenjun Zi, Hangzhou (CN); Nan Shao, Hangzhou (CN); Jingjing Hu, Hangzhou (CN); Liwen Liu, Hangzhou (CN); Xiaotong Zeng, Hangzhou (CN); Ji Zheng, Hangzhou (CN)

(73) Assignee: DEKE MEDTECH (HANGZHOU) INC., Hangzhou (CN)

( * ) Notice: Subject to any disclaimer, the term of this patent is extended or adjusted under 35 U.S.C. 154(b) by 918 days.

(21) Appl. No.: 17/044,241

(22) PCT Filed: Mar. 29, 2019

(86) PCT No.: PCT/CN2019/080586
§ 371 (c)(1),
(2) Date: Sep. 30, 2020

(87) PCT Pub. No.: WO2019/185049
PCT Pub. Date: Oct. 3, 2019

(65) Prior Publication Data
US 2021/0121200 A1  Apr. 29, 2021

(30) Foreign Application Priority Data
Mar. 30, 2018 (CN) .......................... 201810286470.7

(51) Int. Cl.
*A61B 17/34* (2006.01)
*A61B 17/00* (2006.01)
(Continued)

(52) U.S. Cl.
CPC ........ *A61B 17/34* (2013.01); *A61B 17/00234* (2013.01); *A61M 5/00* (2013.01);
(Continued)

(58) Field of Classification Search
CPC ..................... A61M 25/0105; A61M 25/0133
See application file for complete search history.

(56) References Cited

U.S. PATENT DOCUMENTS 7,041,097 B1    5/2006  Webler
2004/0044329 A1*  3/2004  Trudell ............. A61M 25/0133
                                                         604/165.02
(Continued)

FOREIGN PATENT DOCUMENTS

CN          1717265 A      1/2006
CN        106922123 A      7/2017
(Continued)

OTHER PUBLICATIONS

WIPO, State Intellectual Property Office of the P.R., China International Search Authority, International Search Report (with English translation) and Written Opinion dated May 30, 2019 in International Patent Application No. PCT/CN2019/080586, 13 pages.

*Primary Examiner* — Dung T Ulsh
(74) *Attorney, Agent, or Firm* — Inskeep IP Group, Inc.

(57) ABSTRACT

A therapeutic device, therapeutic system and therapeutic method for myocardium repair, wherein the therapeutic device comprises a treatment needle for piercing the heart to release a therapeutant. The treatment needle includes a needle body (5a), the interior of the needle body (5) has a therapeutant conveying cavity, an end of the needle body (5a) is a needle (5b) which can pierce the myocardium and guide the needle body (5a) to pass through the myocardium, and the needle (5b) has a therapeutant output port which is connected to the therapeutant conveying cavity. The therapeutic device enters into the myocardium in a minimally (Continued)

invasive manner to release the therapeutant to the vicinity of the lesion to improve myocardial function or activity and prevent further deterioration of the disease.

18 Claims, 13 Drawing Sheets

(51) Int. Cl.
    *A61M 5/00*     (2006.01)
    *A61M 5/46*     (2006.01)
    *A61M 25/00*     (2006.01)

(52) U.S. Cl.
    CPC .......... *A61M 5/46* (2013.01); *A61M 25/0041* (2013.01); *A61M 25/0084* (2013.01); *A61B 2017/00243* (2013.01); *A61B 2017/00247* (2013.01); *A61M 2025/0089* (2013.01); *A61M 2202/0007* (2013.01); *A61M 2210/125* (2013.01)

(56) References Cited

U.S. PATENT DOCUMENTS

| | | | |
|---|---|---|---|
| 2012/0265186 A1* | 10/2012 | Burger | A61M 25/0138 606/41 |
| 2013/0204138 A1* | 8/2013 | Belohlavek | A61B 8/12 600/463 |
| 2013/0281979 A1* | 10/2013 | Arnim | A61M 25/0147 604/509 |
| 2016/0206853 A1* | 7/2016 | Bolduc | A61M 25/0136 |
| 2018/0153434 A1* | 6/2018 | Tang | A61B 5/0538 |

FOREIGN PATENT DOCUMENTS

| | | |
|---|---|---|
| CN | 206630652 U | 11/2017 |
| CN | 107617140 A | 1/2018 |
| WO | WO2018057940 A1 | 3/2018 |

\* cited by examiner

THERAPEUTIC DEVICE, THERAPEUTIC SYSTEM AND THERAPEUTIC METHOD FOR MYOCARDIUM REPAIR

RELATED APPLICATIONS

This application is the U.S. National Phase of and claims priority to International Patent Application No. PCT/CN2019/080586, International Filing Date Mar. 29, 2019, entitled Therapeutic Device, Therapeutic System And Therapeutic Method For Myocardium Repair, which claims benefit of Chinese Patent Application No. 201810286470.7 filed Mar. 30, 2018; both of which are incorporated herein by reference in their entireties.

TECHNICAL FIELD

This disclosure relates to the treatment of heart disease, in particular to a therapeutic device, therapeutic system and therapeutic method for myocardial repair.

BACKGROUND

Myocardial repair, also known as myocardial failure, refers to the inability of the heart to pump out the blood required by tissue metabolism of the human body. Various diseases often cause the myocardial contractility to be weakened, thereby reducing the blood output of the heart so that the blood is insufficient to meet the requirements of the human body, which will result in a series of symptoms and signs.

Left heart failure occurs most commonly in clinics. With the development of the disease, the lesion site of the left ventricular wall occurs fibrosis or atrophy, and gradually loses elasticity. It is not ideal to use traditional medicine treatment for myocardial repair, and patients affected by heart failure are generally difficult to be treated through surgery.

SUMMARY

The present disclosure provides a device for myocardial repair in a minimally invasive manner, which can enter the myocardium by piercing and release therapeutant.

A therapeutic device for myocardial repair includes a treatment needle for piercing into the myocardium to release therapeutant.

In the present disclosure, the treatment needle can enter the myocardium in a minimally invasive manner to release the therapeutant near the lesion site, so as to improve the myocardial function or activity and prevent further deterioration of the disease.

In one embodiment, the treatment needle includes a needle body, wherein the needle body has a therapeutant delivery chamber inside thereof, and the distal end of the needle body is configured as a needle head that enables to pierce the myocardium and guide the needle body to pass through the myocardium, and wherein the needle head has a delivery therapeutant outlet that communicates with the therapeutant delivery chamber.

The needle body has a therapeutant delivery chamber. In other words, the needle body has a hollow structure. The needle body is generally shaped as a tube, but is not strictly limited to being a round tube. The cross section of the needle body may be shaped in the other forms. However, the outer periphery of the needle bod generally has a smooth edge to prevent scratching the tissue.

The needle head and the needle body may be formed in one piece or separate pieces, and preferably, in one piece. The therapeutant delivery chamber extends to the therapeutant outlet at the distal end of the needle head (the end away from the operator).

In one embodiment, the therapeutant delivery chamber extends in the same diameter towards the distal end to the therapeutant outlet.

In one embodiment, the total length of the needle body and the needle head is enough to at least extend from the outside of the human body to the ventricular free wall.

Since the treatment needle disclosed in the present disclosure enters the thoracic cavity through the intercostal space, and then enters the myocardium, especially the ventricular free wall, to release the therapeutant, so that the length of the treatment needle (the total length of the needle body and the needle head) should meet a certain requirement.

Further preferably, the total length of the needle body and the needle is enough to at least extend from the outside of the human body to the ventricular free wall via the apex.

The treatment needle preferably enters the ventricular free wall via the apex of the heart, so that the length of the treatment needle should also meet the corresponding requirement.

In one embodiment, the total length of the needle body and the needle head ranges from 12 cm to 20 cm.

A treatment needle with a certain range of length can adapt to the individual patients, and the inconvenience of operation and adjustment caused by the excessively long treatment needle can also be avoided.

In one embodiment, the treatment needle has one or more working states depending on the position where the treatment needle is located, and in each working state, the position where the needle head is located is designated as a treatment site.

The needle head should be interpreted as a section of the needle body adjacent to the distal end thereof. The therapeutant outlet may be provided at the axial end of the needle head, or it may be provided at the radial sidewall (that is, the therapeutant is output substantially along the radial direction), or both of which may be combined.

The treatment site corresponds to the position where the needle head is located, and also corresponds to the lesion site in the human body. The treatment site is not limited to one point, but may be a certain range of area, which is also related to the arrangement of the therapeutant outlet. In the case where the therapeutant outlet is configured as a through hole opened at the axial end or side wall, the treatment site of the myocardium is located at the area surrounding the therapeutant outlet. In the case where multiple therapeutant outlets are provided on the side wall of the needle body and distribute along the axial direction, the area of the myocardium that receives the therapeutant may also be slightly larger, in which case, the treatment sites may be regarded as a whole relative to the myocardium.

Different working states correspond to the different positions and postures of the treatment needle in three-dimensional space. The positions and postures of the treatment needle can be changed manually or using peripheral equipment for supporting the operation of the treatment needle, or by the treatment needle itself that is further improved, or by an improved component added to the treatment needle.

In one embodiment, the working state includes at least the initial working state in which the treatment needle has already entered the ventricular free wall, and in the initial working state, the needle head is located in the ventricular free wall.

In one embodiment, in the initial working state, the needle head is located in the ventricular free wall and at the upper area of the midpoint between the atrioventricular sulcus and the apex.

In one embodiment, the initial working state of the treatment needle includes: a first initial working state, in which the needle head is located in the anterior wall of the ventricular free wall; a second initial working state, in which the needle head is located in the side wall of the ventricular free wall; or a third initial working state, in which the needle head is located in the posterior wall of the ventricular free wall.

The needle head has one or more piercing pathways formed by piercing the body surface, passing through the epicardium and then piercing the myocardium, and moving among one or more treatment sites, and each piercing pathway is always located in the myocardium between the endocardium and the epicardium.

The position where the needle head passes through the epicardium is designated as the entry site of piercing, and the one or more piercing pathways extend through the same entry site of piercing. The entry site of piercing should be understood as the position where the needle head has already entered the human body and is in contact with the epicardium, and the needle head can further pierce into the myocardium from the entry site of piercing. The myocardium mainly includes the interventricular septum and the ventricular free wall. Once the needle head pierces the epicardium and enters the myocardium through the entry site of piercing, the needle head would not pierce the epicardium during the movement, and of course, the endocardium is free of being pierced. Even the needle head is transferred to another piercing pathway, the needle head is always in the myocardium between the endocardium and epicardium.

Unless the entry site of piercing is changed, that is, the treatment needle needs to pierce into the myocardium from another position, the treatment needle needs to be completely withdrawn from the myocardium and the epicardium during transferring.

Optionally, in each initial working state of the treatment needle, the needle head respectively corresponds to the first treatment site of one of the piercing pathways. In the same piercing pathway, the remaining treatment sites get closer to the entry site of piercing in sequence relative to the first treatment site.

For example, a piercing pathway is provided from the apex of the heart to the side wall of the ventricular free wall. The first treatment site of the piercing pathway is the farthest from the apex of the heart and is generally located at the upper area of the midpoint between the atrioventricular sulcus and the apex. The rest of the treatment sites gradually get closer to the apex of the heart.

Similarly, one or more piercing pathways are respectively provided on the anterior wall of the ventricular free wall and the posterior wall of the ventricular free wall. Different piercing pathways can extend through the same entry site of piercing or enter through different entry sites of piercing.

In the case where multiple piercing pathways are provided that extend through the same entry site of piercing, after the needle head finishes the movement on all the treatment sites on the same piercing pathway, it would not be withdrawn from the myocardium, and the orientation thereof will be adjusted to further extend along the other piercing pathway until it reaches the first treatment site of the other piercing pathway, that is, the treatment needle is in another initial working state.

The entry site of piercing is interpreted as the position of the needle head, and since the needle head is in contact with the epicardium in this state, it also corresponds to the region of the heart.

The entry site of piercing corresponds to the following region of the heart:
apex;
the anterior wall of the ventricular free wall;
the posterior wall of the ventricular free wall;
the side wall of the ventricular free wall; or
interventricular septum.

The piercing pathways with the same entry site of piercing may extend from the entry site of piercing towards the direction of the myocardial tissue. That is, the piercing pathways need to extend at least in the myocardium.

In one embodiment, one or more sets of treatment sites are provided and located in the ventricular free wall, and the sets of treatment sites are distributed in sequence along the long axis of the heart.

In one embodiment, one or more treatment sites are provided in the same set of treatment sites and are distributed sequentially around the long axis of the heart.

In one embodiment, the treatment sites located on the same piercing pathway are assigned to the same or different sets of treatment sites.

Optionally, the line between the entry site of piercing and the treatment sites on the same piercing pathway extends along the long axis of the heart.

Optionally, the line between the entry site of piercing and the treatment sites on the same piercing pathway is perpendicular to the long axis of the heart in a two-dimensional or three-dimensional space.

Optionally, the line between the entry site of piercing and the treatment sites on the same piercing pathway extends obliquely with respect to the long axis of the heart in a two-dimensional or three-dimensional space.

Optionally, one or more treatment sites are provided on the same piercing pathway.

Preferably, one of the piercing pathways extends along the interventricular septum. For example, both the entry site of piercing and the first treatment site on the piercing pathway are located at the interventricular septum, and the entry site of piercing is in the front of the first treatment site, so that this piercing pathway generally extends in the interventricular septum, but it is not strictly limited to extend along a straight line, and may extend in a curved or turned way as needed.

Optionally, a pulling wire is movably provided in the needle body, wherein the distal end of the pulling wire is connected to the needle head, and the proximal end of the pulling wire extends out of the needle body and functions as a force applying end for pulling the needle head to change the orientation thereof.

The distal end of the pulling wire is located inside the needle body and can be directly connected or indirectly connected to the needle head through a connecting element.

Optionally, the needle head comprises a tip that is fixed with the other part of the needle body by a threaded connection or welding, wherein the tip is provided with a mounting groove at the portion thereof that is connected with the other part of the needle body, and the mounting groove communicates with an inner cavity of the needle body, and wherein the pulling wire extends in the needle body towards the distal end until the pulling wire reaches the mounting groove and is connected to with an inner wall of the mounting groove.

The pulling wire can be directly welded to the inner wall of the installation groove, or indirectly connected through a connecting element. Optionally, the connecting element is fixed in the installation groove by welding or interference fit, and the distal end of the pulling wire is welded and fixed to an outer wall of the connecting element or is clamped and fixed with the connecting element.

Preferably, the connecting element is positively fitted with the mounting groove.

Optionally, the outer wall of the connecting element is provided with a groove for accommodating the distal end of the pulling wire.

Optionally, the therapeutic device further includes a fixed handle that is provided with an intermediate chamber inside thereof; wherein the proximal end of the needle body is inserted into the fixed handle in a sealing manner, and the therapeutant delivery chamber of the needle body communicates with the intermediate chamber; and wherein the fixed handle is provided with an therapeutant inlet that communicates with the intermediate chamber; and wherein the proximal end of the pulling wire extends out of the fixed handle.

The shape of the intermediate chamber is not strictly limited. The needle body and the fixed handle are connected in a sealing manner to avoid leakage. The proximal end of the needle body is opened, which directly extends into and communicates with the intermediate chamber of the fixed handle.

Optionally, the pulling wire extends out of the fixed handle at the proximal end of the fixed handle, and the therapeutant inlet communicates with a side wall of the fixed handle.

In order to avoid interference with the delivery of the therapeutant when operating the pulling wire, the pulling wire can be guided in various directions and the therapeutant inlet can be provided in various orientation. In another optional solution, the therapeutant inlet is located at the axial end surface of the fixed handle at the proximal end, and the pulling wire extends out of the side wall of the fixed handle through the intermediate chamber.

Optionally, the proximal end of the fixed handle is provided with a sealing cap, wherein the pulling wire passes through the sealing cap from the needle body through the intermediate chamber, and engages with the portion of the sealing cap connected therewith in a movable and sealing manner.

The sealing cap can be connected to the proximal end of the fixed handle such as by thread fitting, etc. Since the sealing cap also functions to close the proximal end of the intermediate chamber, the sealing cap and the fixed handle should also be connected in a sealing manner to avoid leakage of the therapeutant.

Optionally, a branch tube communicating with the intermediate chamber is provided on the side wall of the fixed handle, and the end of the branch tube away from the fixed handle is configured as the therapeutant inlet.

The branch tube and the fixed handle may be formed in one piece or separate pieces.

The branch tube may be communicated with an external pipeline and thus connected to an injection device for the therapeutant or an accommodating chamber for accommodating the therapeutant.

During the piercing process, if the orientation of the needle head needs to be adjusted, it is possible to directly pull the pulling wire at the proximal end of the fixed handle, and the pulling wire acts on and bend the needle head to change the piercing direction.

The present disclosure also provides a therapeutic system for myocardial repair, which includes the above therapeutic device.

In one embodiment, a guiding device for positioning the treatment needle before piercing is provided.

The position of the treatment needle can be adjusted by means of the guiding device. The guiding device may be configured as, for example, a manipulator, an adjustment frame, or the like that can move in a three-dimensional space. Different treatment sites of the needle head correspond to different postures of the guiding device. The guiding device can be adjusted and controlled automatically or manually.

In one embodiment, the guiding device also functions to maintain the treatment needle in working states in a hemispherical space during the piercing process.

Assuming that the guiding device generally remains stationary, the treatment needle moves in a certain plane relative to the guiding device. The angle Y between the two limiting positions of the treatment needle is 180 degrees.

If the movement of the guiding device itself or at least the movement of the component supporting the treatment needle is considered, the treatment needle moves in the hemispherical space.

In one embodiment, the treatment needle engages with the guiding device in a slidable and positionable manner.

In one embodiment, the treatment needle is provided with a fixed handle at one end thereof away from the needle head, and engages with the guiding device through the fixed handle.

The guiding device enables and drives the treatment needle to move along a straight line and/or to rotate around a spatial axis to change the position of the treatment needle in the three-dimensional space.

The guiding device may clamp or lock the fixed handle, and thus drive the treatment needle to move and maintain the treatment needle in a stable position.

In one embodiment, the needle body is provided with a scale indicating the position thereof relative to the guiding device.

In one embodiment, a measuring device is further provided for indicating the relative displacement of the needle head between different treatment sites.

The measuring device can be combined with the guiding device or combined with the treatment needle. For example, a certain component of the treatment needle or the guiding device may be provided with a marker or a scale to indicate the change of the position of the treatment needle including the change of the angle of the treatment needle. The measuring device may be provided separately and obtain the spatial position and relative change of the treatment needle through a sensor element. For example, the position of the treatment needle can be obtained by collecting video signals combined with image processing, or directly using a sensor.

In one embodiment, an injection device is further provided, and the injection device communicates with the therapeutant delivery chamber of the needle body through a pipeline for supplying therapeutant.

One or more pipelines may be provided. In the case where multiple pipelines are provided, different therapeutants are respectively provided through the multiple pipelines.

The multiple pipelines may be arranged side by side and formed in separate pieces, or may be formed in one piece. A pipeline with two or more independent chambers can be directly produced through a stretching process.

In one embodiment, the injection device has a control unit that controls the injection time and the injection volume of the therapeutant.

A valve, such as a solenoid valve that can be easily controlled, may be provided on the pipeline. The control unit uses a technique with a combination of software and hardware. A computer can be used and a control program can be preset to drive the solenoid valve to release the therapeutant. In the case where multiple pipelines are used, the control unit can control the pipelines respectively, and provide at least two kinds of therapeutant.

In one embodiment, the injection device is provided with an accommodating chamber for accommodating the therapeutant, and the accommodating chamber delivers the therapeutant to the treatment needle through the pipeline.

In one embodiment, the accommodation chamber contains at least one of the following therapeutants:
filler, drug, myocardial nutrient, and stem cell.

The filler improves the lesion site by physically filling and reinforcement. Preferably, the filler has a certain fluidity before being diluted or in a diluted condition (before injection), so that the filler can enter the human body through the treatment needle.

At least a part of the filler can occupy a certain volume in the human body, and at least the filler would not be completely dissolved by body fluid or blood in the human body and thus lost. Alternatively, no enzyme exists in the human body to decompose the filler and/or no decomposition condition exists in the human body.

The filler is preferably slightly softer than the tissue at the lesion site to avoid the formation of lumps and cause unnecessary damage.

For example, the filler may be in the form of hydrogel, or the like.

The type, proportion, concentration, etc. of the therapeutant can be provided using the existing technique that can improve the myocardial repair. The therapeutant needs to pass through an elongated tube and the treatment needle to release, so that the therapeutant should have a certain fluidity. However, if the therapeutant has a good fluidity, it is easy to lose after entering the myocardium, which would affect the treatment effect. Therefore, it is preferable to choose a therapeutant that has a certain consistency or at least enables to increase the consistency or maintain in a solidified state in the human body to ensure the treatment effect.

In one embodiment, the viscosity of the therapeutant increases after the therapeutant enters the myocardium.

The increase in viscosity of the therapeutant here refers to the decrease in overall fluidity of the therapeutant after entering the myocardium (in the human body) relative to in the pipeline and the treatment needle, to maintain the local concentration of the therapeutant as much as possible.

In one embodiment, the treatment needle corresponds to one or more piercing pathways, and each piercing pathway has one or more treatment sites.

In one embodiment, the control unit sets a corresponding injection time and or injection volume for each treatment site.

In one embodiment, the injection times at the treatment sites are the same or different.

In one embodiment, the injection volumes at the treatment sites are the same or different.

Each piercing pathway corresponds to a set of positions and postures of the treatment needle. The therapeutant at each treatment site has a corresponding injection time and injection volume. The lesions at different treatment sites may be different, so that in practice, the therapeutant is injected and controlled based on the predetermined plan or referring to the results of real-time monitoring.

In one embodiment, the injection volume set for each treatment site by the control unit ranges from 0.05 ml to 1 ml.

The injection volume can be fed back to the control unit through a metering device installed on the pipeline. Alternatively, a delivery pump that can measure the output volume may be provided on the pipeline, and the control unit directly sends corresponding instructions to the delivery pump.

In one embodiment, multiple treatment needles are provided, and each treatment needle corresponds to a piercing pathway.

Although multiple treatment needles are provided, the multiple treatment needles can be respectively controlled and operated sequentially or simultaneously, and perform treatment according to their respective piercing pathways.

In one embodiment, an imaging device is further provided for guiding the treatment needle to pierce.

In one embodiment, the imaging device comprises at least one of ultrasonic, CT, and NMR.

In one embodiment, the imaging device comprises a detection unit that obtains signals of the heart structure, and a display unit that receives the signals from the detection unit and displays the heart structure and indicates one or more piercing pathways.

The imaging device itself is known in the art, and used to monitor the treatment site and display the relative position of the needle body at the treatment site during treatment. The imaging device can collect and process data and perform image display. The imaging device may include the detection unit which is implemented through a sensing element that collects the state parameters of the corresponding position, and the display unit which also displays the information collected by the sensing element while outputting the image, which is more useful to the operation.

In one embodiment, the piercing pathways have a common entry section, and the piercing pathways extend towards different directions from an end of the entry section to form branch sections.

In one embodiment, the entry section extends from the myocardium of the apex to the junction of the apex and the myocardium of the ventricular free wall, and the branch sections extend in the ventricular free wall in different directions.

In one embodiment, the piercing pathway extends into the myocardium through the apex, and the apex is relatively sparse than other nerves, which can avoid excessive stimulation of the heart and causing bad reflexes. Each piercing pathway extends into the ventricular free wall through the apex, and then extends toward the predetermined lesion site.

In one embodiment, the display unit further displays the endocardium and epicardium on both sides of the ventricular free wall for the correction of the piercing pathway.

The piercing pathway should avoid intersecting with the endocardium and the epicardium. The display unit can display the position of the endocardium and the epicardium in real time. If the needle head is found to be too close to any of the endocardium and the epicardium, the operator needs to correct the piercing pathway or stop further piercing of the treatment needle.

In one embodiment, the display unit further functions to indicate one or more treatment sites on each piercing pathway.

In one embodiment, one or more piercing pathways are provided, and the branch sections of the piercing pathways extend into the anterior wall, sidewall, or posterior wall of the ventricular free wall.

In one embodiment, the end of the branch section of the piercing pathway is located at the upper area of the midpoint between the atrioventricular sulcus and the apex.

In one embodiment, a navigation simulation system is further provided for indicating the treatment sites and the positions of the treatment needle.

The navigation simulation system may be one or more of magnetic navigation, infrared navigation, and optical navigation.

In one embodiment, the navigation simulation system performs three-dimensional modeling of the heart in advance, and in use, the navigation simulation system collects the positions of the treatment needle in real time through an imaging device and displays the relative position of the treatment needle in the heart model.

The basic data of the patient's heart can be collected, including four items for myocardial damage (troponin I (TropI), myoglobin (Mb), CK-MB mass, and Brain natriuretic peptide), heart rhythm, routine and 24-hour dynamic electrocardiogram, ultrasonic electrocardiogram, ventricular wall thickness, position and degree of myocardial fiber, the course of the coronary artery, etc., to perform three-dimensional reconstruction of the patient's heart to obtain a heart model. Furthermore, the position of the needle body is connected and displayed in the heart model in real time as real-time monitoring and guidance of the operation.

The collection of basic data can be based on one or more of three-dimensional ultrasonic, CT or NMR, and then the three-dimensional modeling of the heart is performed to show the heart, especially the interventricular septum, ventricular free wall, endocardium and other related structures.

In one embodiment, the navigation simulation system plans the piercing pathway according to the heart model.

Before operation, based on the data of in vitro experiments, animal experiments and clinical records, the corresponding relationship between the treatment area and the release time and release volume of the therapeutant can be calculated, and the piercing pathway of the treatment needle can be planned.

In one embodiment, the heart model shows at least the position of the myocardium and the distribution of the coronary arteries; and the navigation simulation system determines the entry site of piercing according to the position of the myocardium and the distribution of the coronary arteries.

In one embodiment, the heart model shows at least the position of the entry site of piercing and the distribution of the coronary arteries; and the navigation simulation system determines the entry site of piercing according to the position of the entry site of piercing and the distribution of the coronary arteries.

In one embodiment, the position of the entry site of piercing is particularly highlighted, so as to help the needle head to pierce into the myocardium through the entry site of piercing.

In one embodiment, the heart model shows at least the ventricular free wall; and the navigation simulation system indicates the type of the treatment needle based on the thickness of the ventricular free wall.

In one embodiment, the heart model shows at least the endocardium of the ventricle; and the navigation simulation system indicates the type of the treatment needle according to the position of the endocardium to avoid the endocardium.

In one embodiment, the piercing pathway avoids the endocardium and extends in the middle of the thickness of the ventricular free wall. The type of the treatment needle includes length, diameter, etc., which need to be analyzed and determined in advance. The navigation simulation system can visually display the collected data of the position of the treatment needle in combination with the specific type of the treatment needle on the heart model during operation. On the one hand, the operator can judge by himself, and the navigation simulation system can automatically alarm.

In one embodiment, the navigation simulation system collects the position of the treatment needle in real time and compares the position of the treatment needle with the planned piercing pathway, and initiates an alarm when the deviation meets the abnormal condition.

For example, an alarm information can be supplied to the operator by recording the changes of the electrocardiogram during the piercing process of the treatment needle and judging the position of the conduction bundle. It is also possible to predict the next action of the treatment needle based on the current piercing condition, and re-plan the piercing pathway according to the real-time operation to guide the operator and further improve the success rate of the operation.

In one embodiment, the anterior wall, the side wall and the posterior wall of the ventricular free wall are respectively planned with a piercing pathway.

The entire ventricle can be generally covered through three piercing pathways on the anterior wall, side wall and posterior wall of the ventricular free wall.

In one embodiment, multiple treatment sites are planned on the same piercing pathway according to a treatment sequence gradually closer to the entry site of piercing.

The multiple treatment sites on the same piercing pathway get closer to the entry site of piercing according to a sequence of releasing the therapeutant. In other words, after the operation at the previous treatment site is completed, the treatment needle is withdrawn until it reaches the next treatment site. The operations at all treatment sites are completed one by one through intermittent withdrawal of the treatment needle.

In one embodiment, a biopsy needle is further provided for piercing the myocardium for biopsy.

A tissue extraction mechanism of the biopsy needle can be used to obtain the changes of the lesion site before, during and after the operation, thereby evaluating the effect of the operation. The tissue extraction mechanism may extract body fluids, muscles, etc.

The biopsy needle and the needle body may be formed in one or separate pieces. Depending on the physical morphology of the tissue to be extracted, a corresponding extraction means can be used. The component of the tissue extraction mechanism in contact with the tissue and the extraction principle may use existing techniques. As the biopsy needle needs to cooperate with the treatment needle, the structure of the biopsy needle should engage with the elongated needle body. No matter the biopsy needle and the needle body are formed in one or separate pieces, the biopsy needle can be inside the needle body or outside the needle body.

In one embodiment, the biopsy needle and the treatment needle are formed in one piece.

In one embodiment, the biopsy needle corresponds to a piercing pathway that extends from the entry site of piercing to the myocardium.

In one embodiment, an ECG monitoring device is further provided for collecting ECG signals and indicating ECG abnormalities during piercing.

During operation, ECG can be monitored. When ECG shows changes such as premature beats, which can be regarded as an alarming signal, the position where the treatment needle is located at this time may be marked.

The disclosure also provides a therapeutic method for myocardial repair with minimal wound, remarkable curative effect, and almost no bleeding.

A therapeutic method for myocardial repair is implemented based on the therapeutic system for myocardial repair described in this disclosure.

A therapeutic method for myocardial repair, includes: providing a treatment needle, introducing the treatment needle to pierce from the epicardium into the myocardium without passing through the endocardium, and injecting therapeutant for myocardial repair through the treatment needle. The myocardium is ventricular free wall and interventricular septum.

The treatment needle pierces the body surface and enters the myocardium through the epicardium.

The treatment needle enters the myocardium from the epicardium along the short axis of the ventricle or at an acute angle with the short axis of the ventricle.

The treatment needle enters the myocardium from the epicardium along the long axis of the ventricle or at an acute angle with the long axis of the ventricle.

The treatment needle enters the ventricular free wall from the body surface through the epicardium along the short axis of the ventricle, and injects the therapeutant for myocardial repair at one or more sites along a piercing pathway corresponding to the movement of the treatment needle.

The treatment needle enters the posterior ventricular free wall from the body surface through the epicardium along the short axis of the interventricular septum, and injects the therapeutant for myocardial repair at one or more sites along a piercing pathway corresponding to the movement of the treatment needle.

The treatment needle passes through the body surface, the epicardium, and travels in the ventricular free wall via the apex of the heart, and injects the therapeutant for myocardial repair at one or more sites along a piercing pathway corresponding to the movement of the treatment needle.

In one embodiment, a needle head of the treatment needle enters the ventricular free wall from an entry site of piercing along a piercing pathway.

The entry site of piercing corresponds to one or more of the following regions of the heart:
  apex;
  the anterior wall of the ventricular free wall;
  the posterior wall of the ventricular free wall;
  the side wall of the ventricular free wall; and
  interventricular septum.

For example, the treatment needle pierces from the epicardium through the apex into the ventricular free wall.

In one embodiment, the needle head pierces from the body surface, through the intercostal space, and then enters the ventricular free wall from the epicardium via the entry site of piercing.

After the treatment needle enters the myocardium of the apex, it pierces into the ventricular free wall through the junction of the apex and the myocardium of the ventricular free wall, which does not damage the endocardium.

The treatment needle enters the interventricular septum along the central line between the endocardium and the epicardium of the ventricular free wall as much as possible, without damaging the endocardium nor piercing the epicardium again.

The injected therapeutant includes drug, intramyocardial implant or other therapeutant supporting fibrotic myocardium or atrophic myocardium, which can improve the function or activity of the myocardium, and achieve the treatment purpose of improving heart function.

When the treatment needle enters the myocardium of the ventricle free wall through the epicardium, it should avoid coronary arteries as much as possible, and does not pass through the endocardium and the left and right ventricles, and offsets from the conduction bundle of the heart. After the treatment needle pierces into the ventricular free wall, the therapeutant delivered by the treatment needle supports the fibrotic or atrophic myocardium, improves the function or activity of the myocardium, and improves the heart function. The treatment method causes minimal wounds to the human body and the heart, and the abnormal heart response during the operation is small, and the curative effect is remarkable.

In one embodiment, one or more piercing pathways are provided during the treatment according to the movement track of the needle head of the treatment needle, and on each piercing pathway, the needle head of the treatment needle corresponds to one or more treatment sites and releases the therapeutant at each treatment site.

In one embodiment, the needle head corresponds to multiple treatment sites on the same piercing pathway, and first injects the therapeutant at the first treatment site, and then the treatment needle is withdrawn for a predetermined distance and injects the therapeutant at the remaining treatment sites one by one.

For example, the treatment needle may first inject a first dose of the therapeutant at the first treatment site, and then be withdrawn for a certain distance to the second treatment site, and then inject the second dose of the therapeutant at the second treatment site. The same applies to more treatment sites.

In one embodiment, after an appropriate dose of the therapeutant is injected at the previous treatment site, the needle is held for 3 to 6 seconds and then withdrawn along the piercing pathway until the needle head reaches the next treatment site to inject an appropriate dose of the therapeutant, wherein the doses of the therapeutant at different treatment sites may be the same or different.

For example, after the treatment needle injects the first dose of therapeutant at the first treatment site, the treatment needle is held for 3-6 seconds. If the patient is in a stable state, the treatment needle is withdrawn along the piercing pathway by 0.5 cm to 2.0 cm (for example, 1.5 cm), until it reaches the second treatment site and injects a second dose of therapeutant, wherein the first dose and the second dose of therapeutant may be the same or different.

The patient's state can be determined based on ECG parameters and other physical parameters.

On the same piercing pathway, the first treatment site is located at the upper area of the midpoint between the atrioventricular sulcus and the apex.

According to clinical trials and specific case analysis, the treatment needle will usually first reach the upper area of the midpoint between the atrioventricular sulcus and the apex of the ventricular free wall for injection and treatment.

In the same way, the treatment operations for all piercing pathways can be completed.

Optionally, when the needle is transferred to the next piercing pathway which has the same entry site of piercing as the previous piercing pathway, the treatment needle is not withdrawn out of the myocardium. That is, at least the needle head is always located in the myocardium, and is not withdrawn out of the epicardium.

In one embodiment, the piercing process of the treatment needle is performed under the guidance of an imaging device.

In one embodiment, the imaging device is configured as an ultrasonic instrument which scans the long-axis and short-axis views of the heart in a cross manner under the guidance of multi-dimensional ultrasonic, and the piercing pathway is positioned using the ultrasonic guide line.

In one embodiment, the therapeutic method further includes using a guiding device to position the treatment needle before piercing, wherein the guiding device cooperates with the ultrasonic probe to guide the treatment needle to pierce along the ultrasonic guide line.

In one embodiment, the myocardium of the ventricular free wall includes all of the myocardium of the ventricular free wall.

The process of the treatment needle piercing into the ventricular free wall and injection and implantation can be performed under the guidance of an ultrasonic instrument, which can minimize the radiation damage to the human body from the equipment used in the entire operation.

In one embodiment, the ventricular function and the myocardial function are determined by echocardiography.

In one embodiment, the heart function and myocardial function are determined by cardiac MRI.

In one embodiment, an electrocardiogram monitoring is performed simultaneously during the piercing of the treatment needle.

In one embodiment, the therapeutic method further includes preoperative ultrasonic contrast.

In one embodiment, multiple treatment needles are provided, and the multiple treatment needles pierce into the myocardium simultaneously or sequentially before starting the injection device for treatment.

In one embodiment, the therapeutic method further includes preoperative examination and operation program plan.

In one embodiment, the operation program plan includes the following steps:

obtaining a heart model by performing heart segmentation and three-dimensional modeling through medical images;

planning the piercing pathway of the treatment needle according to the entry site of piercing and the distribution of coronary vessels determined by the heart model; and selecting the type of the treatment needle according to the thickness of the ventricular wall.

Preoperative disease assessment and operation program plan are necessary, and intraoperative preventive measures can further prevent surgical risks.

In one embodiment, the myocardial tissue is extracted for myocardial biopsy before the treatment needle releases the therapeutant.

In one embodiment, a biopsy needle is first used for myocardial biopsy, and then the treatment needle is used for treatment, or the treatment needle is directly used for myocardial biopsy, and then for treatment.

In one embodiment, one or more auxiliary treatment drugs are injected through the treatment needle to improve the curative effect.

The present disclosure releases the therapeutant by piercing, which not only has a small trauma but also can directly reach the lesion site, thereby improving the curative effect. The piercing pathway provides opportunity for multiple therapeutic methods. In order to increase the curative effect, therapeutic methods such as drug therapy can be combined to further improve the curative effect of surgery.

DESCRIPTION OF THE EMBODIMENTS

The technical solutions in the embodiments of the present disclosure will be clearly and completely described below in conjunction with the accompanying drawings in the embodiments of the present disclosure. Obviously, the described embodiments are only a part of the embodiments of the present disclosure, not all of the embodiments. Based on the embodiments of the present disclosure, all other embodiments obtained by those skilled in the art without inventive work shall fall within the protection scope of the present disclosure.

It should be noted that when a component is "connected" with another component, it may be directly connected to the other component or may be indirectly connected to another component through a further component. When a component is "provided" on another component, it may be directly provided on another component or may be provided on another component through a further component.

Unless otherwise defined, all technical and scientific terms used herein have the same meaning as commonly understood by those skilled in the art. The terms used in the specification of the present disclosure herein is only for the purpose of describing specific embodiments, not for limiting the present disclosure. The term "and/or" as used herein includes any and all combinations of one or more related listed items.

Figure 1:
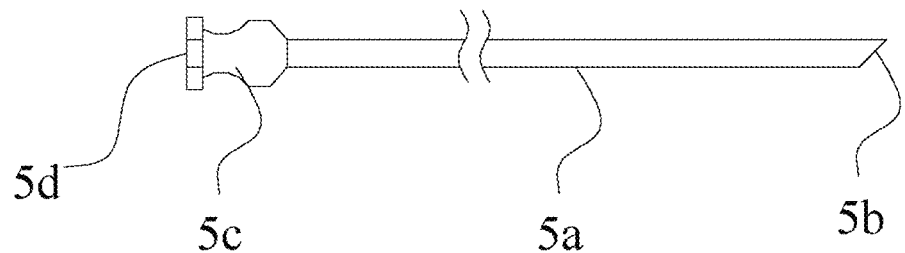
FIG. 1 is a schematic structural view of a therapeutic device for myocardial repair according to one embodiment of the present disclosure.

Referring to FIG. 1, a therapeutic device for myocardial repair provided by the present embodiment includes a treatment needle for piercing into the myocardium to release the therapeutant.

The middle part of the treatment needle is configured as an elongated and hollow needle body 5a. The treatment needle itself may be made of existing metal materials to provide necessary rigidity and elasticity. The needle body 5a is generally shaped as a rounded tube and has a smooth edge on the outer periphery to prevent tissue scratches.

In one embodiment, the inside of the needle body 5a is configured as a therapeutant delivery lumen, and the end of the needle body 5a is configured as a needle head 5b that can pierce the myocardium and guide the needle body to pass through the myocardium. The needle head 5b has a therapeutant outlet communicated with the therapeutant delivery lumen.

The needle head 5b may form a tip by chamfering or the like and may be formed with the needle body 5a into one piece to facilitate processing. The total length of the needle body 5a and the needle head 5a should be enough to at least extend from the outside of the human body to the ventricular free wall to release the therapeutant to the lesion. In one embodiment, the total length of the needle body 5a and the needle head 5a ranges from 12 cm to 20 cm.

The end of the needle body 5a away from the needle head 5b is configured as a therapeutant inlet 5d and communicates with the therapeutant delivery lumen. In other embodiments below, a fixed handle 5c is provided on the outer periphery of the end of the needle body 5a away from the needle head 5b for holding or clamping. In addition, the needle body 5a may be further provided with a scale(s) indicating the position(s) as required.

In different embodiments, the treatment needle may have one or more working states, depending on the position(s) where the treatment needle is located. In each working state, the position where the needle head is located is designated as the treatment site.

Figure 2:
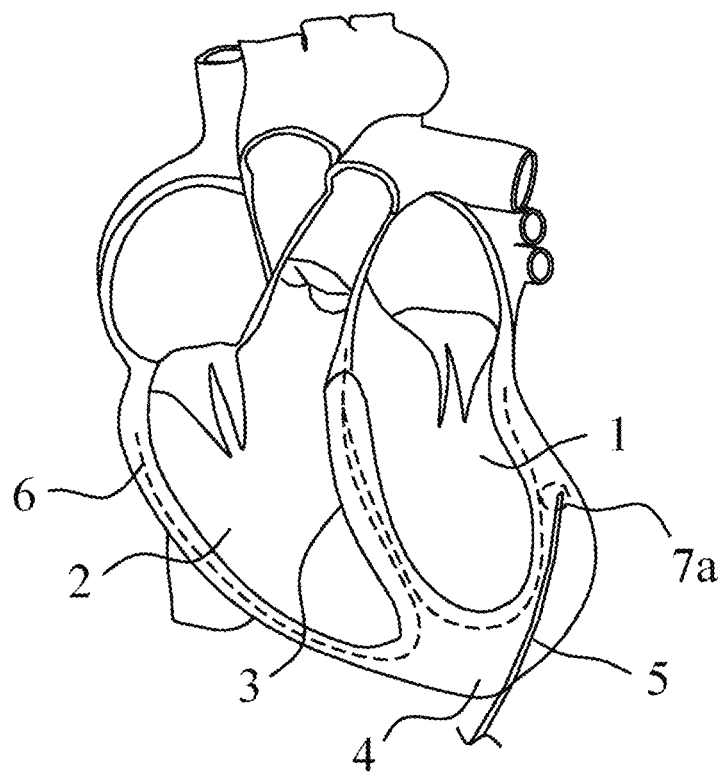
FIG. 2 shows a treatment needle at one treatment site through a piercing pathway.
Figure 3:
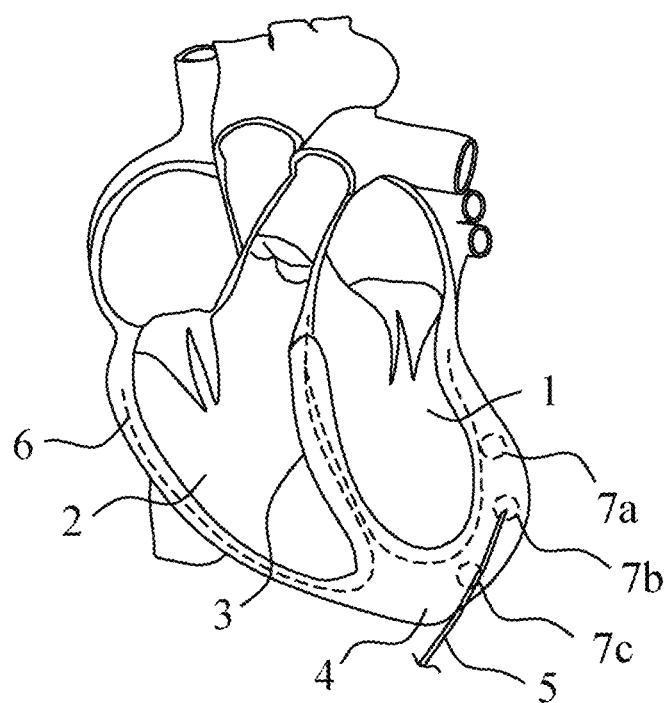
FIG. 3 shows the treatment needle shown in FIG. 2 at a different treatment site.

Referring to FIGS. 2 and 3, the internal structure of the heart is shown, in which the interventricular septum 3 is located between the left ventricle 1 and the right ventricle 2, and a conduction bundle 6 (shown by the dashed line) extends in the interventricular septum 3 and the ventricular free wall.

Depending on the movement pathway of the needle head, in different embodiments, the needle head has one or more piercing pathways formed by piercing the body surface, passing through the epicardium, and then piercing the myocardium, and moving among one or more treatment sites. Each piercing pathway is always located in the myocardium between the endocardium and epicardium.

The position where the needle head passes through the epicardium is designated as the entry site of piercing. One or more piercing pathways extend through the same entry site of piercing. In other embodiments, it is also possible to pass through the epicardium via different entry sites of piercing as needed.

In different embodiments, the position of the heart corresponding to the entry site of piercing may be the apex, the anterior wall of the ventricular free wall, the posterior wall of the ventricular free wall, the sidewall of the ventricular free wall, or the interventricular septum.

In one embodiment, the working state includes at least the initial working state in which the treatment needle has already entered the ventricular free wall. In the initial working state, the needle head is located in the ventricular free wall. In the preferred embodiment, in the initial working state, the needle head is located in the ventricular free wall and at the upper area of the midpoint between the atrioventricular sulcus and the apex. In each initial working state of the treatment needle, the needle head is located at the first treatment site of the corresponding piercing pathway.

In a preferred embodiment, in the same piercing pathway, the remaining treatment sites get closer to the entry site of piercing in sequence relative to the first treatment site.

In this embodiment, the needle head of the treatment needle 5 may pierce the ventricular free wall through the apex 4 until it reaches the treatment site 7a. After the therapeutant is released at the treatment site 7a, the needle head is withdrawn for a certain distance and reaches the treatment site 7b to release the therapeutant, and similarly, then releases the therapeutant at the treatment site 7c. The piercing pathway starts from the entry site of piercing at the apex and extends to the treatment site 7c, the treatment site 7b, and the treatment site 7a in sequence.

In other embodiments, the needle head may pierce the ventricular free wall through other positions, and is not strictly limited to pierce the ventricular free wall through the apex 4.

Different treatment sites correspond to the different postures of the treatment needle 5, i.e., the different working states of the treatment needle 5. The treatment site 7a where the therapeutant is first released may be regarded as the initial treatment site, which corresponds to the initial working state of the treatment needle 5. The needle head shown in FIG. 2 is located in the side wall of the ventricular free wall. In other embodiments, depending on the piercing pathway, the initial treatment site of the needle head may be located in the anterior wall of the ventricular free wall; or the initial treatment site of the needle head may be located in the posterior wall of the ventricular free wall.

Figure 4:
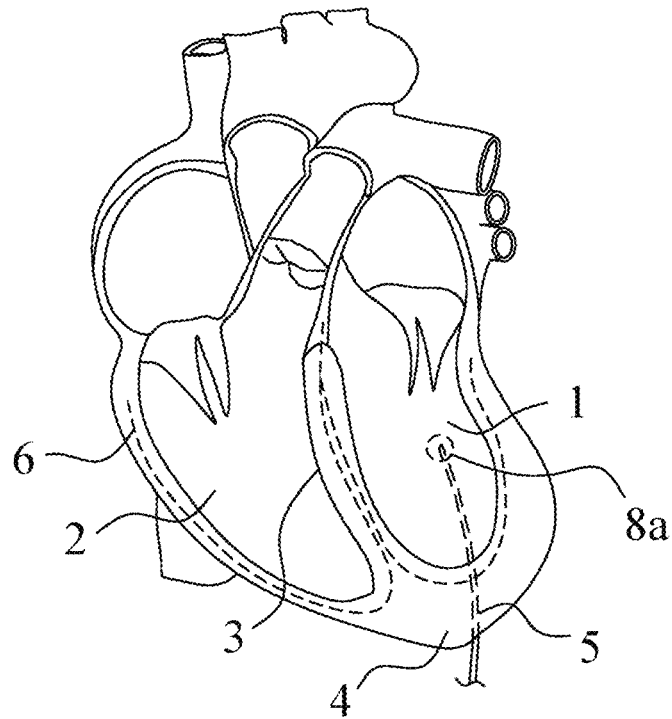
FIG. 4 shows a treatment needle at one treatment site through another piercing pathway.
Figure 5:
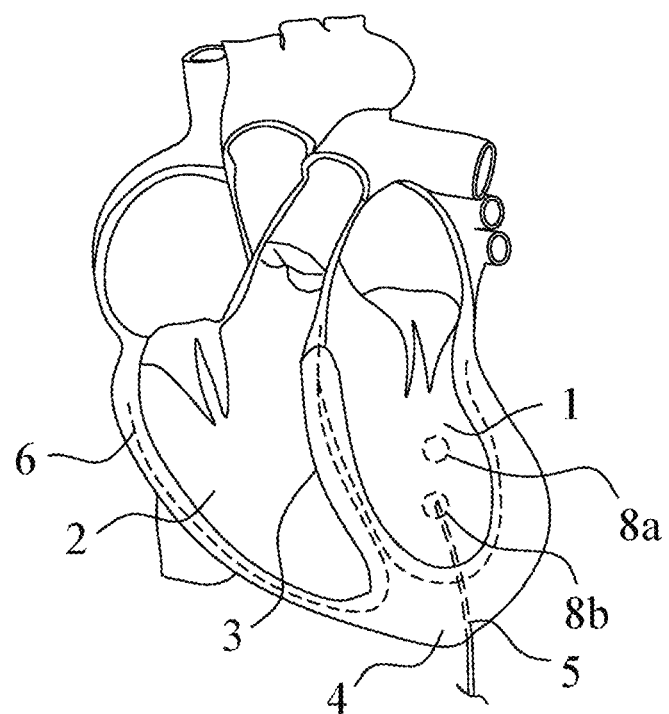
FIG. 5 shows the treatment needle shown in FIG. 4 at a different treatment site.

Referring to FIGS. 4 and 5, in the piercing pathway of another embodiment, the initial treatment site of the needle head (i.e., the treatment site 8a) is located in the posterior wall of the ventricular free wall. There are two treatment sites provided in this piercing pathway, one is the treatment site 8a, and the other is the treatment site 8b which is slightly lower relative to the treatment site 8a. During operation, the therapeutant is released at the treatment site 8a and the treatment site 8b in order.

Figure 6:
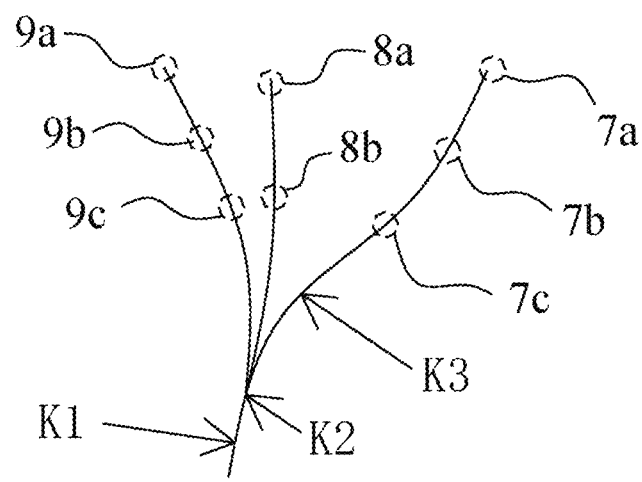
FIG. 6 shows a distribution of treatment sites on three piercing pathways.

Referring to FIG. 6, in another embodiment, multiple piercing pathways are provided which have a common entry section K1. The multiple piercing pathways extend towards different directions from the end of the entry section K1 (where the point K2 is located) to form branch sections. In other words, the multiple piercing pathways are branched into a tree shape from the position of the point K2. Each piercing pathway may include multiple treatment sites. For example, one of the piercing pathways K3 extends into the side wall of the ventricular free wall, and includes treatment sites 7c, 7b and 7b.

Another piercing pathway extends into the posterior wall of the ventricular free wall, and includes treatment sites 8b and 8a.

A further piercing pathway extends into the anterior wall of the ventricular free wall, and includes treatment sites 9c, 9b and 9a.

The entry section K1 is preferred to extend from the myocardium of the apex to the junction of the apex and the myocardium of the ventricular free wall, and then the branch sections extend in the ventricular free wall in different directions.

Figure 7:
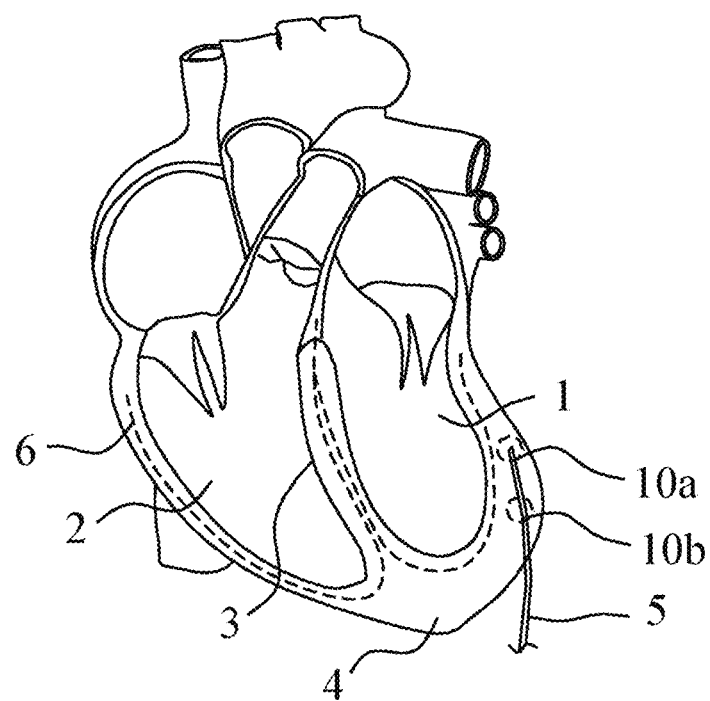
FIG. 7 shows a treatment needle at one treatment site through a piercing pathway with a different starting point.

Referring to FIG. 7, in another embodiment, the entry site of piercing is slightly offset to the sidewall of the ventricular free wall, instead of in the myocardium of the apex. The piercing pathway includes a treatment site 10b and a treatment site 10a.

Figure 8:
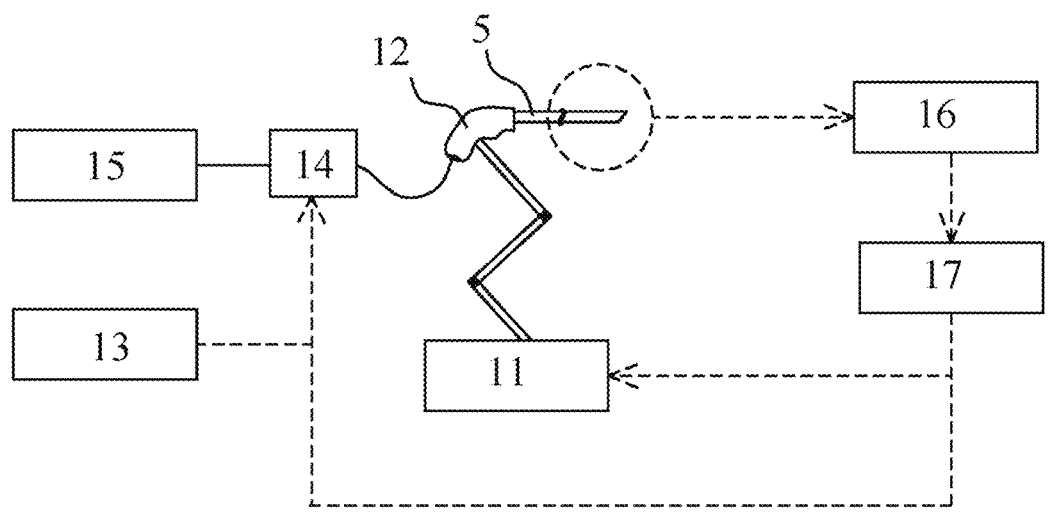
FIG. 8 is a schematic diagram of a therapeutic system for myocardial repair according to one embodiment of the present disclosure.

Referring to FIG. 8, a therapeutic system for myocardial repair provided in this embodiment includes any of the therapeutic devices provided in the embodiments (separately, or in combination) herein, and each therapeutic device includes at least a treatment needle 5.

In another embodiment, the therapeutic system is further provided with a guiding device 11 that positions the treatment needle 5 before piercing and holds the treatment needle in corresponding working states during piercing.

The guiding device 11 may be configured as a manipulator, an adjusting frame, or the like that is capable of moving in three-dimensional space. The guiding device 11 is provided with a holder 12 that engages with and limits the fixed handle of the treatment needle. The three-dimensional position of the treatment needle is changed through the holder 12. In one embodiment, the guiding device can hold the treatment needle in different working states in the hemispherical space during piercing.

In order to adjust the relative position between the treatment needle and the guiding device, in one embodiment, the treatment needle engages with the guiding device in a slidable and fixable manner. In other words, the relative position between the treatment needle and the guiding device can be adjusted, and the relative position can be maintained by using a conventional locking mechanism after adjustment.

In another embodiment, the therapeutic system is further provided with an injection device, and the injection device communicates with the treatment needle through a pipeline(s) for supplying the therapeutant.

In one embodiment, the injection device further includes an accommodating chamber 15 for accommodating the therapeutant. The accommodating chamber 15 supplies the therapeutant to the treatment needle through a pipeline(s).

In the state of use, the accommodating chamber 15 contains at least one of the following therapeutants:

Filler, drug, myocardial nutrient, and stem cell.

In a preferred embodiment, the filler is in the form of hydrogel.

The accommodating chamber 15 contains the therapeutant. If various types of therapeutant are required, various sets of the accommodating chamber and the corresponding pipeline can be provided in parallel and communicate with the treatment needle through a multi-way valve.

The type, proportion, concentration, etc. of the therapeutant can be provided using the existing technique that can improve the myocardial repair. In a preferred embodiment, the viscosity of the therapeutant increases after entering the myocardium, which helps to better maintain the local concentration of the therapeutant.

In one embodiment, the injection device is provided with a control unit for controlling the injection time and the injection volume of the therapeutant. For an automatic control, the pipeline is provided with a control valve 14. The control unit 13, which is computer-based and presets control program, drives the control valve 14 to open or close to control the release of the therapeutant. The injection times and injection volumes of the therapeutant at the treatment sites may be the same or different.

For example, the control unit 13 may set the injection volume of the therapeutant for each treatment site as 0.05 ml to 1 ml. The injection volume of the therapeutant may be fed back to the control unit through a metering device installed on the pipeline.

Since each piercing pathway may have multiple treatment sites, in one embodiment, the control unit may set a corresponding injection time and/or injection volume of the therapeutant for each of the treatment sites. The injection times of the therapeutant at the treatment sites may be the same or different. Similarly, the injection volumes of the therapeutant at the treatment sites may be the same or different.

In another embodiment, the therapeutic system is also provided with an imaging device 16 for a real-time display of the treatment site and guiding the treatment needle to pierce. Specifically, the imaging device 16 may use at least one of the following techniques: ultrasonic, CT, and nuclear magnetic.

In one embodiment, the imaging device includes a detection unit that obtains signals reflecting the structure of the heart, and a display unit that receives the signals from the detection unit and displays the structure of the heart and indicates one or more piercing pathways.

In one embodiment, the display unit further displays the endocardium and the epicardium on both sides of the ventricular free wall for the correction of the piercing pathway.

In one embodiment, the display unit also functions to indicate one or more treatment sites on each piercing pathway.

In another embodiment, the therapeutic system is also provided with a navigation simulation system 17 that indicates the treatment sites and the positions of the treatment needle. The navigation simulation system 17 performs three-dimensional modeling of the heart in advance, and in use, it collects the position of the treatment needle in real time through the imaging device and displays the relative position of the treatment needle in the heart model.

In one embodiment, the navigation simulation system 17 plans the piercing pathway according to the heart model.

In one embodiment, the navigation simulation system 17 plans the treatment site according to the heart model, and the function of the control unit 13 may be integrated with the navigation simulation system 17 to directly control the release time and release volume of the therapeutant.

The heart model shows at least the position of the myocardium and the distribution of the coronary arteries. The navigation simulation system determines the entry site of piercing according to the position of the myocardium and the distribution of the coronary arteries.

In other embodiments, if the needle needs to pierce through the apex, the heart model shows at least the position of the apex and the distribution of the coronary arteries. The navigation simulation system determines the entry site of piercing according to the position of the apex and the distribution of the coronary arteries.

The heart model shows at least the ventricular free wall. The navigation simulation system indicates the type of the treatment needle according to the thickness of the ventricular free wall.

In one embodiment, the heart model shows at least the endocardium of the ventricle. The navigation simulation system indicates the type of the treatment needle which can avoid the endocardium according to the position of the endocardium.

In one embodiment, the heart model further includes the ventricular free wall; the navigation simulation system can also select the type of the treatment needle according to the thickness of the ventricular free wall.

In order to achieve various functions, in one embodiment, the heart model shows the position of the apex, the distribution of the coronary arteries, the ventricular free wall, the endocardium, the epicardium, etc. Before operation, based on the data of in vitro experiments, animal experiments and clinical records, the corresponding relationship between the treatment area and the release time and release volume of the therapeutant can be calculated, and the piercing pathway of the treatment needle can be planned. The function of the control unit 13 can be integrated into the navigation simulation system at the corresponding treatment site to directly control the release time and release volume of the therapeutant.

During operation, the navigation simulation system can visually display the collected data about the position of the treatment needle in combination with the specific type of the treatment needle on the heart model. The operator may judge by himself. In other embodiments, the navigation simulation system may collect the position of the treatment needle in real time and compare it with the planned piercing pathway. In the case where the deviation meets the abnormal condition, the navigation simulation system may indicate an alarm, and it may even directly drive the control valve 14.

In another embodiment, the therapeutic system is further provided with a biopsy needle for piercing the myocardium for biopsy. A tissue extraction mechanism of the biopsy needle can be used to obtain the changes of the lesion site before, during and after the operation, thereby evaluating the effect of the operation. The tissue extraction mechanism may extract body fluids, muscles, etc. In a preferred embodiment, the biopsy needle and the treatment needle may form in one piece. Similarly, the biopsy needle also has a piercing pathway through the entry site of piercing into the myocardium. In another embodiment, the therapeutic system is also provided with an ECG monitoring device that collects ECG signals and can indicate ECG abnormalities during piercing. During operation, ECG can be monitored. When ECG shows changes such as premature beats, which can be regarded as an alarming signal, the position where the treatment needle is located at this time may be marked.

The present embodiment provides a therapeutic method for myocardial repair, which is an ultra-minimally invasive therapeutic method. The therapeutic method includes the following steps: providing the treatment needle according to the embodiments herein, in combination or alone, piercing the treatment needle from the epicardium into the myocardium without passing through the endocardium, and injecting the therapeutant for myocardial repair through the treatment needle.

For example, the treatment needle may be pierced from the epicardium into the ventricular free wall through the intercostal space, and the therapeutant injected or implanted by the treatment needle can support the fibrotic or atrophic myocardium and improve the myocardial function or activity, thereby improving the heart function and repairing myocardium.

The therapeutic method mainly includes the implementation of the surgical treatment. In other embodiments, the therapeutic method may further include at least one step of medical history information collection, preoperative examination, and operation program plan as required.

During the treatment, the piercing pathway, and the treatment site, etc. can be referred to using that of the treatment needle 5 of the therapeutic device according to the embodiments (in combination or alone) herein.

In addition, during the implementation of the therapeutic methods according to the embodiments herein, the therapeutic device and the therapeutic system according to the embodiments (in combination or alone) herein can be used.

The steps are described in detail below. In one embodiment, one or more steps can be implemented, and the numbers below are only for distinction rather than limiting the implementation sequence.

1. Medical History Information Collection and Preoperative Examination.

The patient's body, especially the heart's functions, can be examined in detail through the preoperative examination to monitor the patient's specific conditions, such as the thickness of the ventricular free wall, the pressure difference of the left ventricular outflow tract, the obstruction and so on. The items of the preoperative examination are shown in the following table.

| Items of preoperative examination | |
|---|---|
| Items of examination | Purpose of examination |
| Four items for myocardial damage: troponin I (TropI), myoglobin (Mb), CK-MB mass, and Brain natriuretic peptide | Determine the degree of myocardial damage of the patient |
| Routine electrocardiogram (ECG) | Determine the activity of the heart and the presence of arrhythmia |
| 24 hour dynamic electrocardiogram (Holter) | Determine the presence of nonsustained ventricular tachycardia and assessing the risk for sudden death |
| Ultrasonic electrocardiogram | Determine the heart function, the thickness of the ventricular wall, and the pressure difference of the left ventricular outflow tract of the patient, and the presence of systolic dysfunction, and dilated heart failure |
| Cardiac MRI | Determine the thickness of the ventricular wall, the site and the degree of myocardial fiber |
| Coronary artery CTA | Determine the presence of the coronary artery disease and the course of the coronary artery to avoid piercing the coronary artery |
| Other routine inspection and examination before operation | Assessing the body condition of the patient comprehensively, and excluding contraindication of operation |

The instruments for the examination may use the related instruments in the prior art, and the specific steps for the examination and the use of the instruments will not be repeated here.

2. Operation Program Plan.

After the preoperative examination, the operation program can be planned according to the thickness of the ventricular free wall of the patient and the specific condition of the heart movement. Specifically, the operation program plan includes the following steps:

Planning the piercing pathway: piercing the treatment needle from the body surface through the intercostal space, and then from the epicardium into the ventricular free wall via the apex. The treatment needle should travel between the endocardium and the epicardium of the ventricular free wall, without damaging the endocardium thereby avoiding influence on and contact with the conduction bundle below the endocardium of the ventricular free wall, and also avoiding piercing the epicardium to damage the coronary artery or cause hydropericardium. The piercing pathway of the needle preferably avoids the intercostal arteries and veins and the coronary arteries and veins at the apex. For patients with ventricular aneurysm at the apex, the piercing pathway of the needle should avoid damaging the ventricular aneurysm.

In various embodiments, the piercing way can be planned using a manual method or using the therapeutic system herein or combining the both.

When planning the piercing pathway, it should be noted that:
1. The piercing pathway of the needle should avoid the intercostal arteries and veins and the coronary arteries and veins at the apex;
2. For patients with ventricular aneurysm at the apex, the piercing pathway of the needle should avoid damaging the ventricular aneurysm;
3. The piercing direction should extend in the central line of the long axis of the interventricular septum in the apical four-chamber view as much as possible;
4. The treatment needle should travel along the middle of the myocardium of the free wall, thereby avoiding contact with the conduction bundle below the endocardium of the ventricular free wall.

Determining the treatment site and the dose of the therapeutant: determining one or more treatment sites according to the thickness and the movement of the ventricular free wall, planning the piercing pathway by prioritizing the treatment sites, and planning the treatment time and the dose of the therapeutant according to the piercing pathway and the thickness and the movement of the ventricular free wall.

3. The Implementation of the Surgical Treatment

The surgical treatment includes the following steps:

(1) ECG Monitoring Throughout the Surgical Treatment.

In order to observe the changes of the patient's heart rate and rhythm during the surgical to timely detect arrhythmia such as ventricular premature beat, atrial fibrillation or even ventricular tachycardia, and to determine whether the patient has myocardial ischemia and electrolyte imbalance, etc, ECG monitoring is performed throughout the surgical treatment to observe the patient's ECG data all the time.

(2) Positioning Before Piercing and Performing Ultrasonic Contrast.

Under the guidance of ultrasonic, the positioning is performed before piercing by a probe for the heart through a guide line in the long-axis or short-axis view. For the non-standard apical four-chamber or five-chamber view, the positioning is performed before piercing using the guide line, and the piercing pathway through the apex is selected. A technique of CDFI (color Doppler flow imaging) with low-speed is used to avoid damage to the blood vessels on the surface of the heart when piercing the apex.

(3) Piercing and Inserting the Treatment Needle.

The treatment needle is positioned and inserted through the guiding device. The needle head of the treatment needle passes from the surface of the body through the intercostal space, and then from the epicardium into the ventricular free wall via the entry site of piercing.

In one embodiment, the needle is inserted through the parasternal intercostal space, and passes through the skin, subcutaneous tissue, pericardium, outer pericardium, apex in sequence, and enters into the upper area of the midpoint between the atrioventricular sulcus of the ventricular free wall and the apex along the long axis of the ventricular free wall. During the process of piercing, a real-time ultrasonic monitoring is performed. In another embodiment, it is also possible to adopt other piercing pathways.

After the treatment needle pierces into the myocardium via the apex, the treatment needle should enter into the ventricular free wall from the junction of the apex and the myocardium of the ventricular free wall, and travel between the endocardium and the epicardium of the ventricular free wall as much as possible, without damaging the endocardium, the conduction bundle below the endocardium, the epicardium, and the coronary arteries extending in the epicardium. The treatment is performed at the target area by injection or implantation of the therapeutant.

After the needle head of the treatment needle reaches the predetermined treatment site, the injection device is activated to release the therapeutant through the treatment needle. The therapeutant includes but is not limited to one or any combination of drugs, intramyocardial implants, and others.

During the treatment, depending on the movement track of the needle head of the treatment needle, one or more piercing pathways may be provided. On each piercing pathway, the needle head of the treatment needle corresponds to one or more treatment sites and releases therapeutant at each treatment site.

In one embodiment, on the same piercing pathway, the needle head corresponds to multiple treatment sites. First, the therapeutant is injected at the first treatment site, and then the treatment needle is withdrawn for a predetermined distance, and the therapeutant is injected at the remaining treatment sites one by one.

After the injection at one of the treatment sites is completed, the treatment needle is first withdrawn for a certain distance to the next treatment site, and the injection device is activated again for treatment, thereby realizing treatment for multiple different treatment sites.

In a preferred embodiment, after an appropriate dose of the therapeutant is injected at the previous treatment site, if the patient is in a stable state for 3 to 6 seconds, the needle is withdrawn or inserted by 0.5 to 2.0 cm along the piercing pathway until the needle head reaches the next treatment site to inject an appropriate dose of the therapeutant, wherein the doses of the therapeutant at different treatment sites may be the same or different.

In one embodiment, after injection is performed at all the treatment sites on a certain piercing pathway, the treatment needle can be transferred to the next piercing pathway, and the treatment needle does not need to be completely withdrawn from the epicardium In other embodiments, the treatment needle can be completely withdrawn from the epicardium during the transferring process.

(4) Removing the Treatment Needle.

After the injection is performed at all the piercing pathways, the treatment needle can be withdrawn, and ultrasonic contrast can be performed again to show the myocardial thickening at the injected areas.

Figure 9A:
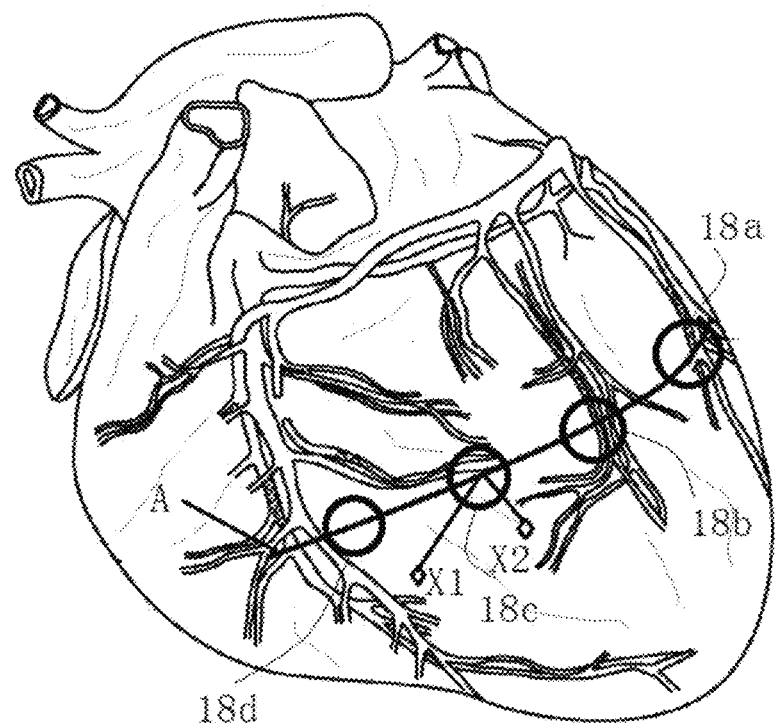
FIGS. 9a-9d respectively show the distributions of treatment sites according to several embodiments.

Referring to FIG. 9a, when an interventional treatment is performed, multiple treatment sites can be provided as required. In this embodiment, four treatment sites are provided, i.e., treatment sites 18a, 18b, 18c, 18d, which are distributed at the strip-shaped area A, and generally distributed around the long axis of the heart. Taking the treatment site 18c as an example, the treatment needle can be pierced into the myocardium at the position of the epimyocardium corresponding to the entry site of piercing X1. The connection line between the entry site of piercing X1 and the treatment site 18c may extend along the long axis of the heart, or the short axis of the heart, or may extend obliquely relative to the long axis of the heart.

The extension direction of the piercing pathway is related to the entry direction of the treatment needle. Since the heart is not shaped as a regular geometry, the pathway that the needle head of the treatment needle travels from the entry site of piercing to the treatment site is not strictly limited to be shaped as a straight line, it may be slightly curved or turned. When the piercing pathway is referred to extend along the long axis or the short axis of the heart, it should be interpreted that the piercing pathway extends along the long axis or the short axis of the heart as a whole, and it is not strictly limited to extend along the long axis or the short axis of the heart in parts.

Figure 9B:
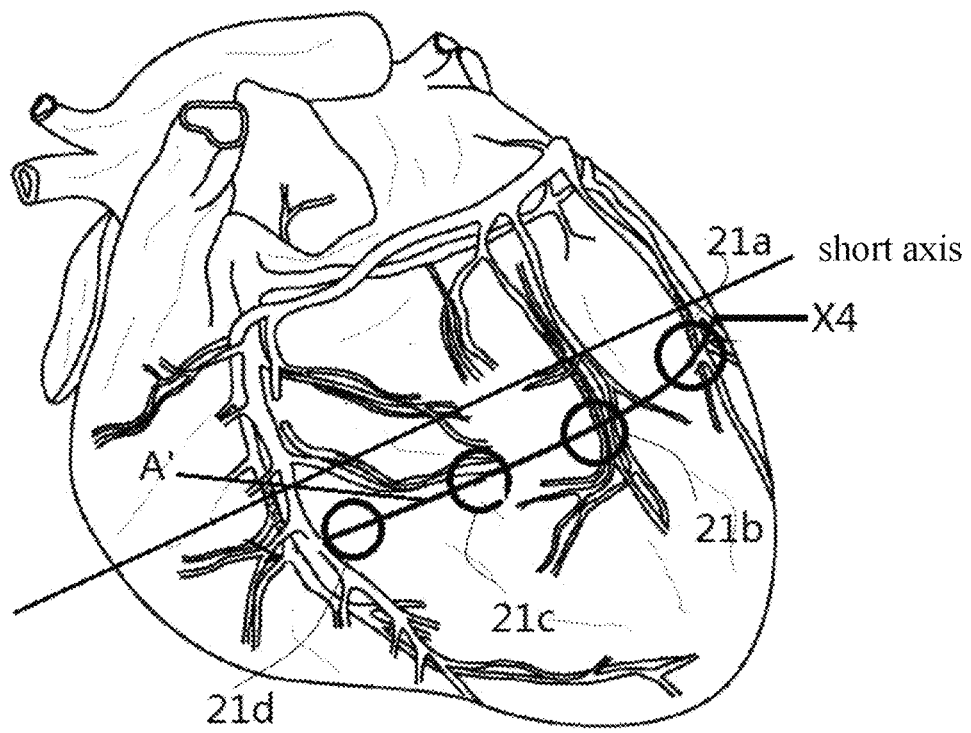

In general, if the entry site of piercing is located at the apex of the heart, the piercing pathway generally extends along the long axis of the heart. If the entry site of piercing is located at one side of the heart, and the piercing pathway then extends around the long axis of the heart (for example, as shown in FIG. 9b to FIG. 9e), so that the piercing pathway generally extends along the short axis of the heart. Referring to FIG. 9b, in one embodiment, when piercing, the treatment needle may enter through the intercostals space below the armpit, and then enter into the ventricular wall through the entry site of piercing X4 of the epicardium of the left ventricle. Treatment sites 21a, 21b, 21c, and 21d are arranged on the treatment strip A'. The treatment needle can be bent first by a pulling wire and travel along the ventricular wall to the treatment site 21d farthest from the entry site of piercing X4 to inject therapeutant. After the injection at the treatment site 21d is completed, the treatment needle is withdrawn to the treatment site 21c to inject therapeutant, and similarly, to the treatment site 21b to inject therapeutant, and then, to the treatment site 21a to inject therapeutant, and finally, it is withdrawn to the epicardium. This piercing pathway generally extends along the short axis of the heart.

Figure 9C:
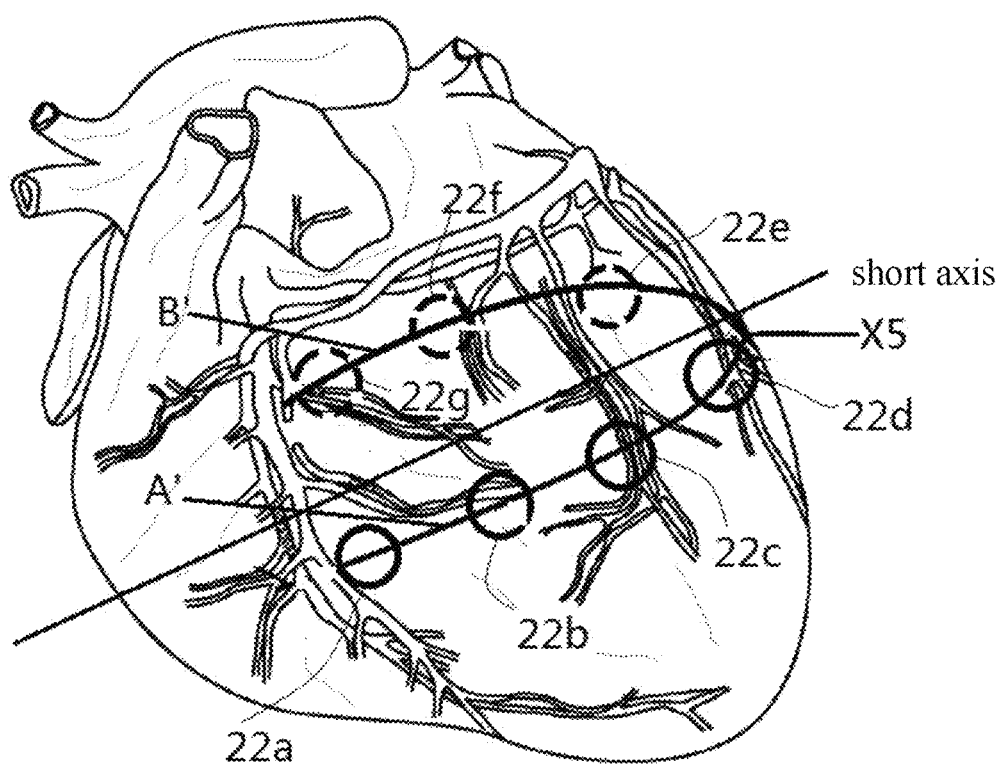

Referring to FIG. 9c, in one embodiment, two treatment strips are planned in advance, namely treatment strip A' and treatment strip B', wherein the treatment strip A' is located at the anterior wall of the left ventricle, and the treatment strip B' is located at the posterior wall of the left ventricle. The treatment strip A' includes treatment sites 22a, 22b, 22c, and 22d, and the treatment strip B' includes treatment sites 22e, 22f, and 22g.

The treatment needle first pierces into the entry site of piercing X5 of the epicardium, and then is bent to enter into the treatment site 22a farthest from the entry site of piercing X5 for injection, and then is withdrawn to inject therapeutant at the treatment site 22b, the treatment site 22c, and the treatment site 22d in sequence. At this time, the treatment needle is withdrawn to the entry site of piercing X5, and then, is transferred to the other piercing pathway, and injects therapeutant at the treatment site 22g, the treatment site 22f, the treatment site 22e on the treatment strip B' in sequence, and finally, is withdrawn from the entry site of piercing X5. During transferring to the other piercing pathway, the needle head of the treatment needle may always be hold in the ventricular wall, that is, between the epicardium and the endocardium. Both the two piercing pathways in this embodiment generally extend along the short axis of the heart.

Figure 9D:
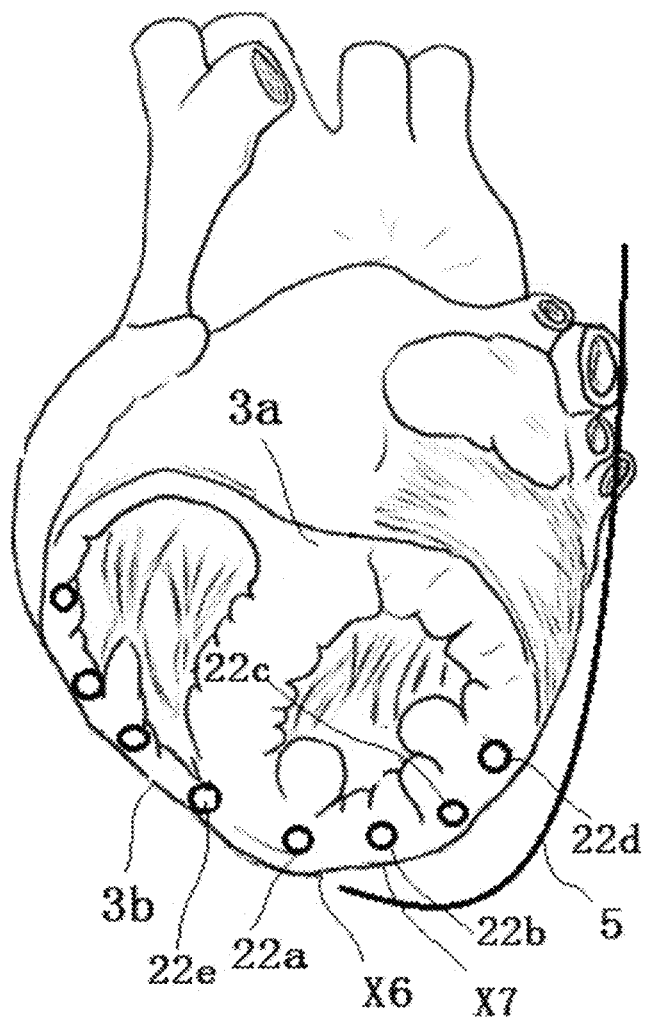

Referring to FIG. 9d, in one embodiment, some treatment sites are located at the posterior wall of the ventricle 3b. After the treatment needle 5 is bent, it extends from the anterior wall of the ventricle 3a to the posterior wall of the ventricle 3b around the outer periphery of the heart.

The treatment needle first enters into the treatment site 22a through the entry site of piercing X6 for injection, and then, is withdrawn to the epicardium. Thereafter, the treatment needle is withdrawn outside the heart to the area near the entry site of piercing X7, and pierces the epicardium to enter into the treatment site 22b via the entry site of piercing X7 for injection. In a similar way, the treatment needle respectively enters into the treatment site 22c and the treatment site 22d for injection. In other words, once the treatment needle needs to be transferred to another piercing pathway, the treatment needle will be completely withdrawn from the epicardium.

After that, the treatment needle 5 extends to the area near the treatment site 22e along the other side, that is, the left side of the heart shown in the FIG. 9d. In a similar way as the side including the treatment sites 22a to 22d, the treatment needle injects at the four treatment sites on the side where the treatment site 22e is located in sequence.

In the same way, the treatment needle can also be pierced through another entry site. For example, the treatment needle can pierce into the myocardium at a position of the epicardium corresponding to the entry site of piercing X2.

Figure 10:
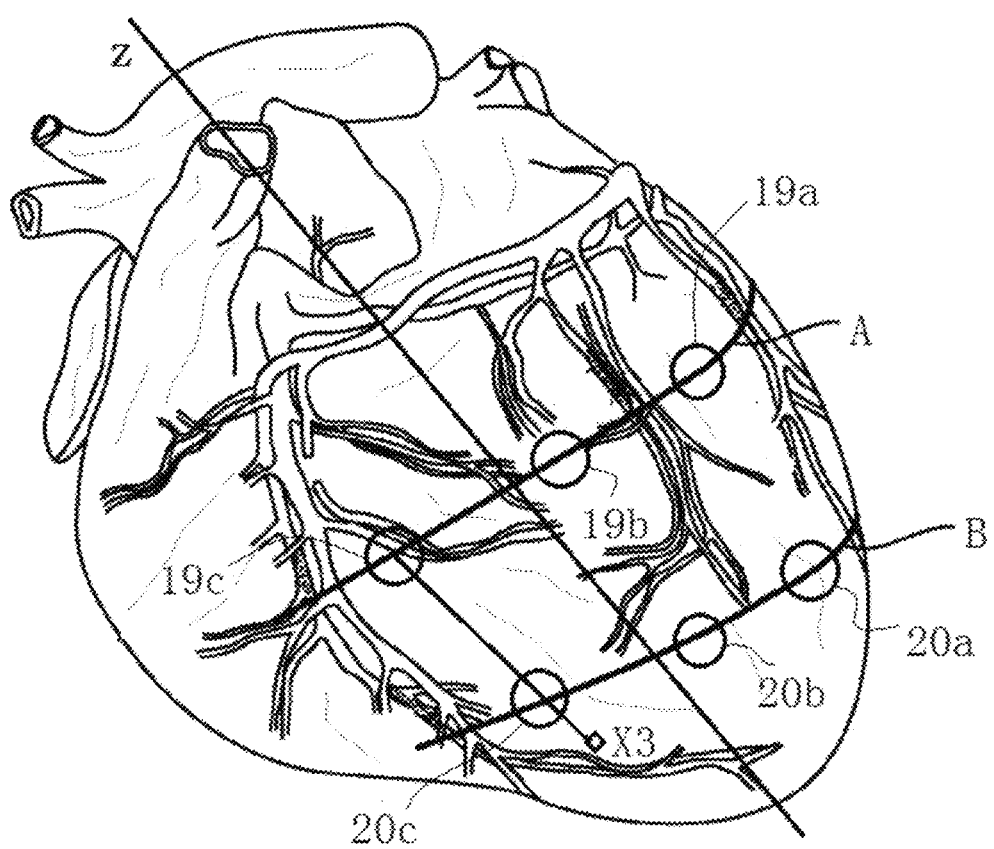
FIG. 10 shows a distribution of multiple groups of treatment sites.

Referring to FIG. 10, in one embodiment, two sets of treatment sites are arranged in the direction of the long axis Z of the heart, one of which includes treatment sites 19a, 19b, and 19c, which are distributed in the strip-shaped area A, and the other includes treatment sites 20a, 20b, and 20c, which are distributed in the strip-shaped areas B. Each strip-shaped area, i.e., the same set of treatment sites, is generally distributed around the long axis Z of the heart.

Each set of treatment sites is not limited to being on the same piercing pathway. For example, the treatment site 19c and the treatment site 20c may be on the same piercing pathway. The treatment needle pierces into the myocardium at the position of the epicardium corresponding to the entry site of piercing X3. After reaching the treatment site 19c, the treatment needle is in the initial working state, and first injects the therapeutant, such as hydrogel, at the treatment site 19c, and then is withdrawn to the treatment site 20c to inject the therapeutant.

Figure 11A:
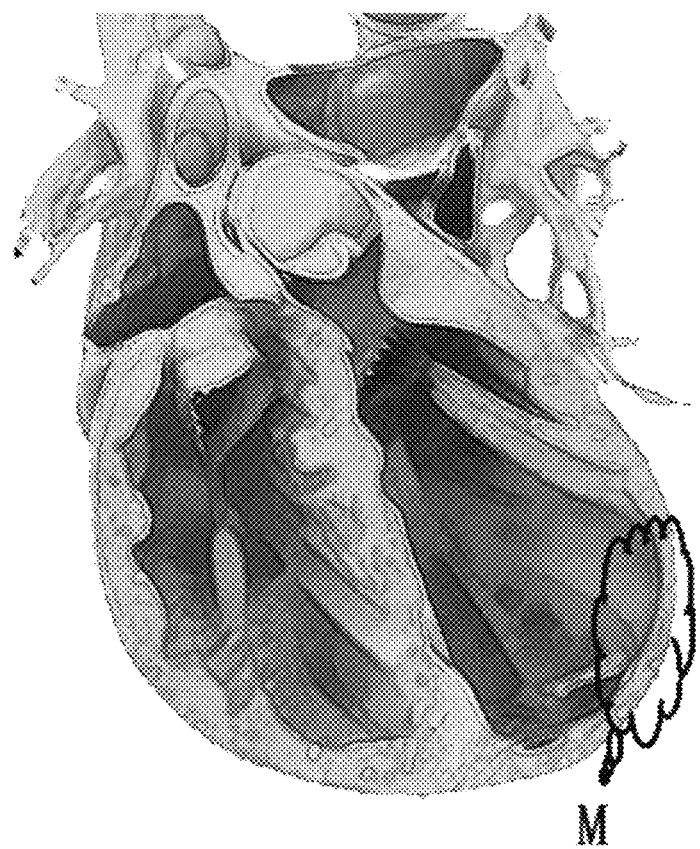
FIG. 11a shows the ventricular wall before treatment.
Figure 11B:
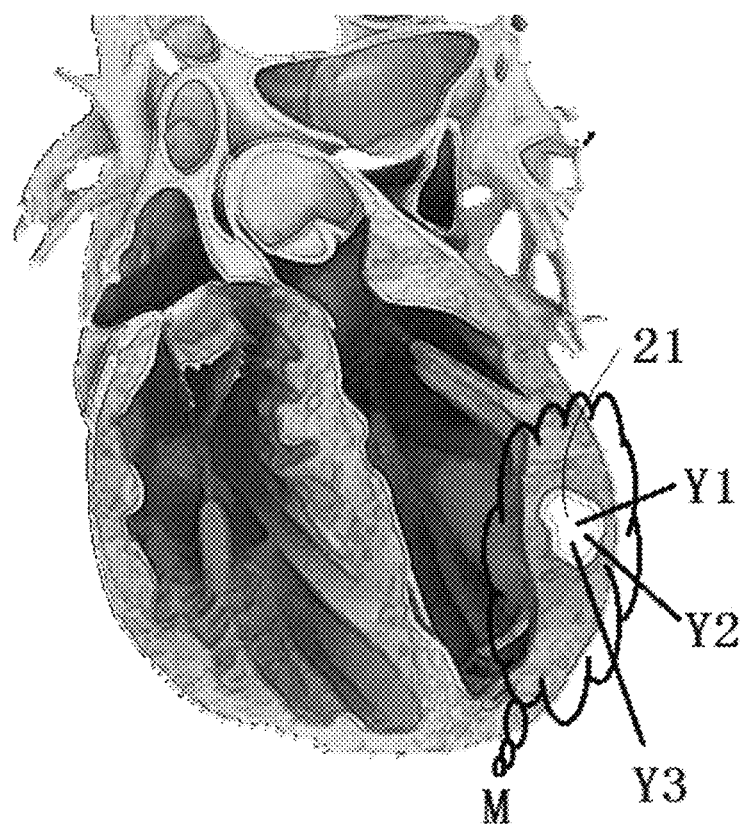
FIG. 11b shows the ventricular wall in FIG. 11a after treatment.

Referring to FIGS. 11a and 11b, in one embodiment, the ventricular wall at the lesion site M where heart failure occurs is significantly thinner, and the ventricular wall at the lesion site M is thickened as a whole after injection of hydrogel at the treatment site 21. The piercing direction of the treatment needle to the treatment site 21, that is, the connection line between the entry site of piercing and the treatment site may extend along the following direction:

Along the short axis of the heart, that is, the extension direction of the line Y1;

Along a direction that is inclined for a certain angle relative to the long axis of the heart, such as for 30 degrees, that is, the extension direction of the line Y2; or Along the long axis of the heart, that is, the extension direction of the line Y3.

Figure 12:
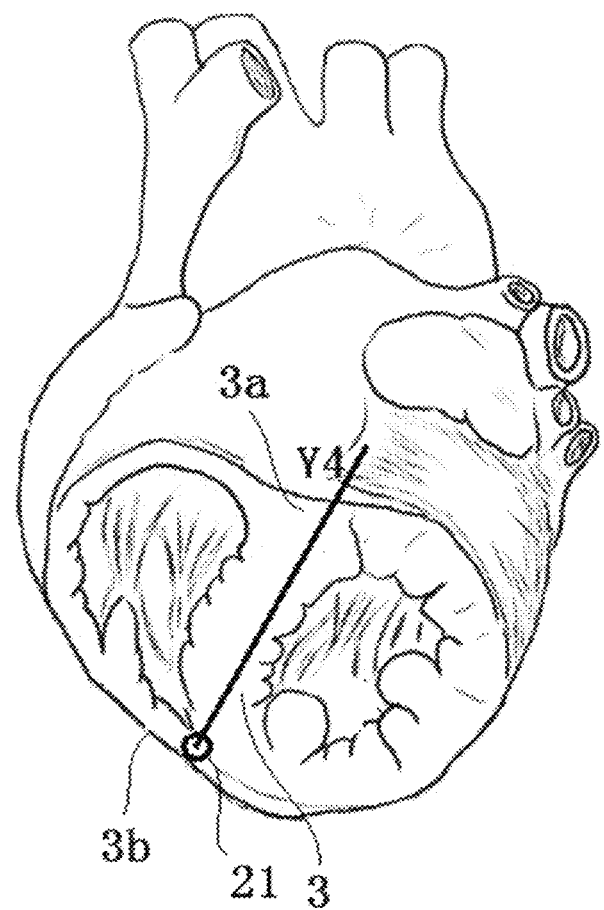
FIG. 12 shows another piercing pathway.

Referring to FIG. 12, in one embodiment, within the ventricular wall where heart failure occurs, treatment sites are located on the side of the heart where the posterior wall 3b of the ventricle is located. A piercing pathway can be selected, which extends from the side where the anterior wall 3a is located to the interventricular septum 3, i.e., along the line Y4 as shown in the FIG. 12, until the treatment site 21 on the side where the posterior wall 3b of the ventricle is located. It can be seen from the FIG. 21 that the piercing pathway generally extends in the interventricular septum 3, and should also avoid piercing the endocardium.

Figure 13:
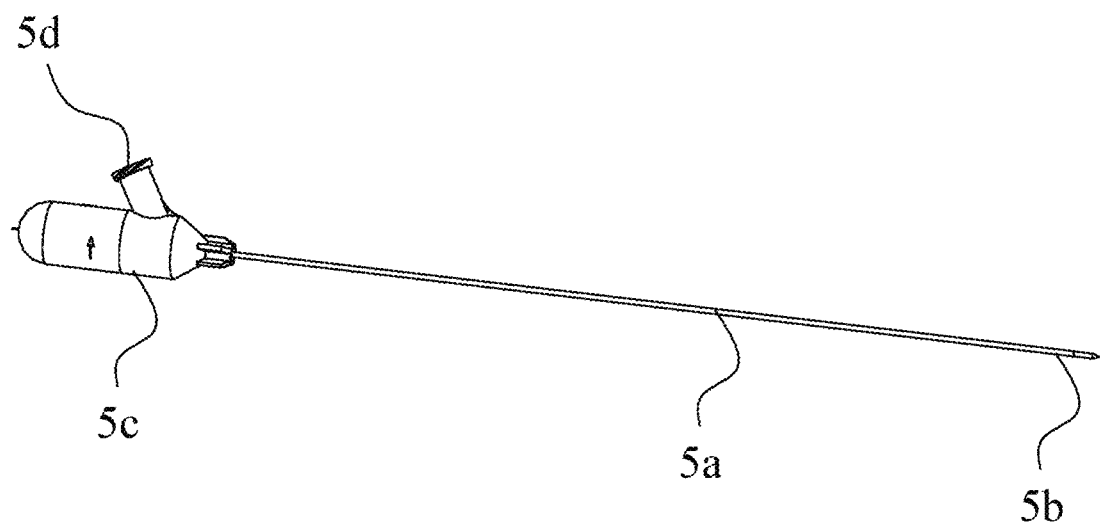
FIG. 13 is a schematic structural view of a therapeutic device for myocardial repair according to another embodiment of the present disclosure.
Figure 14:
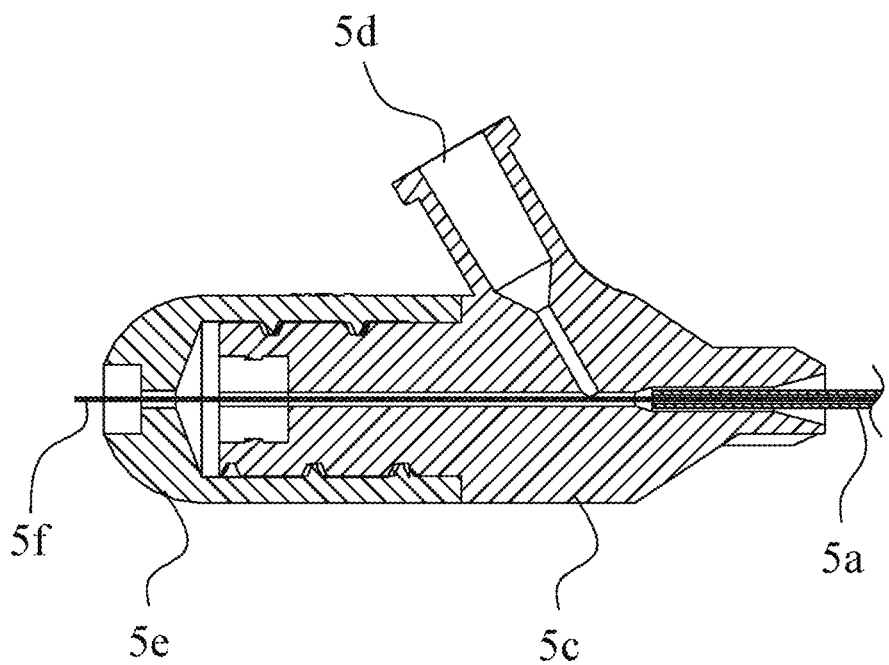
FIG. 14 is a cross-sectional view of the fixed handle portion of the treatment needle shown in FIG. 13.
Figure 15:
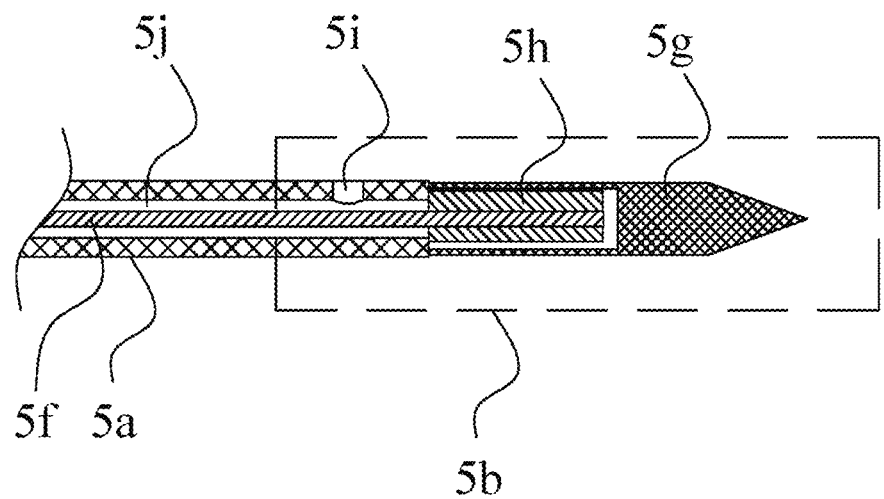
FIG. 15 is a cross-sectional view of the tip of the treatment needle shown in FIG. 13.

Referring to FIGS. 13 to 15, this embodiment provides a therapeutic device for myocardial repair which includes a treatment needle. The treatment needle has an elongated and hollow needle body 5a, and the distal end of the needle body 5a is configured as a needle head 5b that can pierce the myocardium and guide the needle body to pass through the myocardium. A fixed handle 5c is located at one end of the needle body 5a away from the needle head 5b.

In order to facilitate the adjustment of the piercing direction of the treatment needle in the myocardium, in one embodiment, a pulling wire 5f is provided for guiding the needle head 5b to bend. For example, the pulling wire 5f may movably pass through the interior of the needle body. The distal end of the pulling wire 5f is connected to the needle head, and the proximal end of the pulling wire 5f extends out of the needle body and functions as a force applying end for pulling the needle head to change the orientation thereof.

In one embodiment, the needle head 5b includes a tip 5g, and the end of the tip 5g may be fixed to the other part of the needle body 5 (the part of the needle body excluding the tip 5g) by welding or the like. The tip 5g may be provided with a mounting groove at the portion thereof that is connected with the other part of the needle body, and the mounting groove communicates with the inner cavity of the needle body. The pulling wire extends in the needle body towards the distal end until it reaches the mounting groove and is connected to with the inner wall of the mounting groove.

In one embodiment, the pulling wire is connected with the inner wall of the mounting groove through a connecting element 5h that is fixed in the needle head 5b. The pulling wire 5f extends in the needle body, and the distal end of the pulling wire 5f is fixed with the connecting element 5h such as by welding or tight-fitting. In a preferred embodiment, a groove for accommodating the distal end of the pulling wire is provided on the outer wall of the connecting element.

The proximal end of the pulling wire 5f extends in the needle body 5a until it extends out of the proximal end of the needle body 5a. A gap 5j is reserved between the inner wall of the needle body 5a and the outer wall of the pulling wire 5f, and the gap 5 functions as a therapeutant delivery chamber flowing.

In order to avoid interference with the distal end of the pulling wire 5f, an therapeutant outlet 5i is provided in the side wall of the needle body at the needle head 5b.

In order to avoid interference with the proximal end of the pulling wire 5f, in one embodiment, the proximal end of the pulling wire 5f directly extends out of the end of the fixed handle 5c. The side wall of the fixed handle 5c is provided with a branch tube, and an therapeutant inlet 5d is provided on the branch tube.

In one embodiment, the fixed handle 5c is provided with an intermediate chamber that communicates with the therapeutant delivery chamber. The therapeutant inlet 5d communicates with the intermediate chamber through the branch tube. The needle body 5a is inserted to the distal end of the fixed handle 5c and communicates with the intermediate chamber. The branch tube communicates with the intermediate chamber at the side wall of the fixed handle 5c.

In order to avoid leakage of the therapeutant, in one embodiment, the proximal end of the fixed handle 5c engages with a sealing cap in threaded connection. The proximal end of the pulling wire 5f extends out of the sealing cap through the intermediate chamber and engages with the portion of the sealing cap connected therewith in a sealing manner.

The therapeutant enters the intermediate chamber in the fixed handle 5c via the therapeutant inlet 5d through the branch tube, and then enters the gap 5j between the needle body 5a and the pulling wire 5f, and is transported to the distal end of the needle body 5a, and finally is delivered to the lesion site of the myocardium through the therapeutant outlet 5i on the side wall of the needle head 5b.

During the piercing process, if the orientation of the needle head 5b needs to be adjusted, the pulling wire 5f can be directly pulled at the proximal end of the fixed handle 5c, and the pulling wire 5f acts on the needle head 5b to bend the needle head 5b so as to change the piercing direction.

Figure 16:
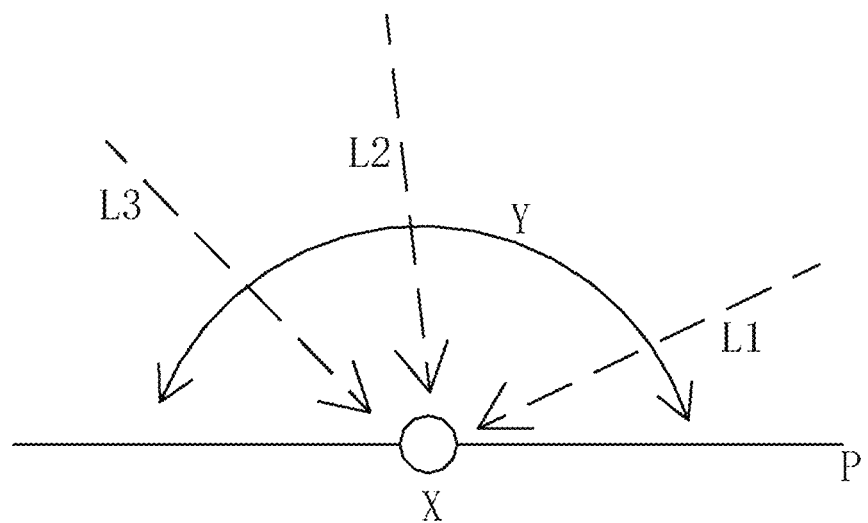
FIG. 16 shows the variation of the positions of the treatment needle.

Referring to FIG. 16, a reference horizontal plane P is assumed at a height X of the heart, and the treatment needle can move in the hemispherical space above the reference horizontal plane P under the guidance of the guiding device and can be maintained at a predetermined angle. Assuming that the guiding device generally remains stationary, the movement of the treatment needle can be simplified as a two-dimensional movement in a certain plane. The angle Y between the two limiting positions of the treatment needle is 180 degrees. FIG. 16 shows the schematic movement lines L1, L2 and L3 at different positions of the treatment needle in the two-dimensional movement.

The technical features of the above embodiments can be combined arbitrarily. In order to make the description concise, all possible combinations of the technical features in the above embodiments are not described. However, as long as the combination of these technical features does not have contradiction, this combination of these technical features should be regarded as falling within the scope of this specification.

The above disclosures are only specific implementations of the disclosure, but the disclosure is not limited thereto, and those skilled in the art can make various changes and modifications to the disclosure without departing from the spirit and scope of the disclosure. Obviously, these changes and modifications should fall within the protection scope required by this disclosure. In addition, although some specific terms are used in this specification, these terms are only for convenience of description and do not constitute any special restrictions on this disclosure.

What is claimed is:

1. A therapeutic device for myocardial repair, comprising:
   a treatment needle for piercing into a myocardium to release therapeutant, which comprises:
   a needle body, which has a therapeutant delivery chamber inside thereof, and
   a needle head, which is located at a distal end of the needle body for piercing the myocardium and guiding the needle body to pass through the myocardium, wherein the needle head has a delivery therapeutant outlet that communicates with the therapeutant delivery chamber, and
   a pulling wire,
   wherein the pulling wire is movably provided in the needle body, and wherein a distal end of the pulling wire is connected to the needle head, and a proximal end of the pulling wire extends out of the needle body and functions as a force applying end for pulling the needle head to change an orientation thereof;
   a fixed handle which has an intermediate chamber inside thereof, and
   wherein a proximal end of the needle body is inserted into the fixed handle in a sealing manner, and the therapeutant delivery chamber of the needle body communicates with the intermediate chamber; and the proximal end of the pulling wire extends out of a proximal end of the fixed handle;
a sealing cap provided at the proximal end of the fixed handle, and
wherein the pulling wire passes through the sealing cap from the needle body through the intermediate chamber and engages with the sealing cap in a movable and sealing manner.

2. The therapeutic device for myocardial repair according to claim 1, wherein a total length of the needle body and the needle head ranges from 12 cm to 20 cm.

3. The therapeutic device for myocardial repair according to claim 1, wherein the needle head comprises a tip that is fixed with the needle body, wherein the tip is provided with a mounting groove into which the distal end of the pulling wire extends.

4. The therapeutic device for myocardial repair according to claim 3, wherein the needle head further comprises a connecting element that is received in the mounting groove, and the distal end of the pulling wire is fixed to the connecting element.

5. The therapeutic device for myocardial repair according to claim 1, wherein the therapeutic device further comprises a branch tube which is provided at aside wall of the fixed handle and communicates with the intermediate chamber of the fixed handle, and wherein an end of the branch tube away from the fixed handle is configured as an therapeutant inlet that communicates with the intermediate chamber of the fixed handle.

6. A therapeutic system for myocardial repair, comprising the therapeutic device according to claim 1.

7. A therapeutic method for myocardial repair, comprising:
providing the therapeutic device according to claim 1,
introducing the treatment needle to pierce from an epicardium into the myocardium without passing through an endocardium, and
injecting therapeutant for myocardial repair through the treatment needle.

8. The therapeutic method for myocardial repair according to claim 7, wherein the treatment needle is introduced via a body surface to pierce from the epicardium into the myocardium, and wherein the myocardium comprises atrial free wall, ventricular free wall, and/or interventricular septum.

9. The therapeutic method for myocardial repair according to claim 7, wherein the treatment needle is introduced to pierce the myocardium from the epicardium along an short axis of a ventricle or at an acute angle with the short axis of the ventricle, or
the treatment needle is introduced to pierce the myocardium from the epicardium along a long axis of the ventricle or at an acute angle with the long axis of the ventricle.

10. The therapeutic method for myocardial repair according to claim 7, wherein the needle head of the treatment needle is introduced into a ventricular free wall via an entry site of piercing along a piercing pathway, and the entry site of piercing corresponds to one or more of the following regions of a heart: apex, an anterior wall of the ventricular free wall, a posterior wall of the ventricular free wall, a side wall of the ventricular free wall, and interventricular septum.

11. The therapeutic method for myocardial repair according to claim 10, wherein one or more piercing pathways are provided during a therapeutic process according to a movement track of the needle head of the treatment needle, and wherein on each piercing pathway, the needle head of the treatment needle corresponds to one or more treatment sites and releases the therapeutant at each treatment site.

12. The therapeutic method for myocardial repair according to claim 11, wherein the needle head corresponds to multiple treatment sites on each piercing pathway, and the therapeutant is first injected at a first treatment site, and then the treatment needle is withdrawn for a predetermined distance and the therapeutant is then injected at remaining treatment sites one after another.

13. The therapeutic method for myocardial repair according to claim 12, wherein after an appropriate dose of the therapeutant is injected at a previous treatment site, when a patient is in a stable state for 3 to 6 seconds, the needle is then withdrawn or inserted by 0.5 to 2.0 cm along the piercing pathway until the needle head reaches a next treatment site, and an appropriate dose of the therapeutant is then injected at the next treatment site, wherein the doses of the therapeutant at different treatment sites are the same or different.

14. The therapeutic method for myocardial repair according to claim 12, wherein on each piercing pathway, the first treatment site is located at an upper area of a midpoint between an atrioventricular sulcus and the apex.

15. The therapeutic method for myocardial repair according to claim 11, wherein when the needle is transferred to a next piercing pathway which has a same entry site of piercing as a previous piercing pathway, the treatment needle is remained within the myocardium.

16. The therapeutic method for myocardial repair according to claim 10, wherein a piercing process of the treatment needle is performed under the guidance of an imaging device, and the imaging device scans the heart in a cross manner along a long and short axes of the heart for determining the piercing pathway.

17. The therapeutic method for myocardial repair according to claim 16, further comprising using a guiding device to position the treatment needle before piercing, and the guiding device cooperates with the imaging device and guides the treatment needle to pierce into the myocardium.

18. The therapeutic method for myocardial repair according to claim 10, further comprising a step of operation program plan, wherein the operation program plan comprises the following steps:
obtaining a heart model by performing heart segmentation and three-dimensional modeling through medical images;
planning the piercing pathway of the treatment needle according to the entry site of piercing and a distribution of coronary vessels determined by the heart model; and
selecting a type of the treatment needle according to a thickness of the ventricular wall.

* * * * *